US007094401B1

(12) United States Patent
Worman et al.

(10) Patent No.: US 7,094,401 B1
(45) Date of Patent: Aug. 22, 2006

(54) HCV CORE PROTEIN BINDING AGENTS FOR TREATMENT OF HEPATITIS C VIRUS INFECTION

(75) Inventors: Howard J. Worman, New York, NY (US); Naoto Mamiya, Aichi (JP)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/407,432

(22) Filed: Sep. 29, 1999

(51) Int. Cl.
*A61K 38/43* (2006.01)
(52) U.S. Cl. ............................... 424/94.1; 424/196.11; 435/5; 435/7.1; 435/183; 435/188; 435/15; 435/193
(58) Field of Classification Search ............. 424/159.1, 424/161.1, 94.1, 196.11; 435/5, 7.1, 183, 435/188, 15, 193
See application file for complete search history.

(56) References Cited

OTHER PUBLICATIONS

Owsianka and Patel, Virology 257, 330-340 (1999), May 10, 1999.*
Alter, M.J. (1997) "Epidemiology of Hepatitis C" *Hepatology*, 26:625-655 (Exhibit 2).
Chien, C., et al. (1991) "The two-hybrid system: a method to identify and clone genes for proteins that interact with a protein of interest" *Proc. Natl. Acad. Sci. U.S.A.*, 88:9578-9582 (Exhibit 3).
Choo, Q.-L., et al. (1989) "Isolation of a cDNA clone derived from blood-borne nonA, nonB viral hepatitis genome" *Science*, 244:359-362 (Exhibit 4).
Choo, Q.-L., et al. (1991) "Genetic organization and diversity of the hepatitis C virus" *Proc. Natl. Acad. Sci. U.S.A.*, 88:2451-2455 (Exhibit 5).
Chuang, R.-Y., et al. (1997) "Requirement of the DEAD-box protein Ded1p for messenger RNA translation" *Science*, 275:1468-1471 (Exhibit 6).
Fields, S., and Song, O. (1989) "A novel genetic system to detect protein—protein interactions" *Nature*, 340:245-246 (Exhibit 7).
Fukushi, S., et al. (1997) "The sequence element of the internal to ribosome entry site and a 25-kilodalton cellular protein contribute efficient internal initiation of translation of hepatitis C virus RNA" *J. Virol.*, 71:1662-1666 (Exhibit 8).
Gee, S. L., and Conboy, J. G. (1994) "Mouse erythroid cells express multiple putative RNA helicase genes exhibiting high sequence conservation form yeast to mammals" *Gene*, 140:171-177 (Exhibit 9).
Hsieh, T.-Y. (1998) "Hepatitis C virus core protein intgeracts with hetrogeneous nuclear ribonucleoprotein K" *J. Biol. Chem.*, 271, 17651-17659 (Exhibit 10).
Kato, N., et al. (1990) "Molecular cloning of the human hepatitis C virus genome from Japanese patients with non-A, non-B hepatitis" *Proc. Natl. Acad. Sci. U.S.A.*, 87:9524-9528 (Exhibit 11).
Kim, J. L., et al. (1998) "Hepatitis C virus NS3 RNA helicase domian with a bound oligonucleotide : the crystal structure provides insights into the mode of unwinding" *Structure*, 6:89-100 (Exhibit 12).

Kim, D. W., et al. (1994) "Trans-suppression of gene expression by hepatitis C viral core protein" *Jpn. J. Med. Sci. Biol.*,47:211-220 (Exhibit 13).
Kuo, G., et al. (1989) "An assay for circulating antibodies to a major etiological virus of human non-A, non-B hepatitis" *Science*, 244:359-363 (Exhibit 14).
Lanford, R. E., et al. (1993) "Analysis of hepatitis C virus capsid, E1, and E2/NS1 proteins expressed in insect cells" *Virology*, 197:225-235 (Exhibit 15).
Leroy, P., et al. (1989) "The protein encoded by a murine male germ cell-specific transcript is a putative ATP-dependent RNA helicase" *Cell*, 57:549-559 (Exhibit 16).
Liang, T. J. (1998) "Combinaton therapy for hepatitis C Infection" N. Eng. J. Med., 339; 1549-1550 (Exhibit 17).
Mamiya,N., et al. (1997) "Epidemiology, prevention, clinical features and therapy of hepatitus B, C, and G" Current Opinion in Infectious Diseases., 10:390-397 (Exhibit 18).
Matsumoto, M., et al. (1996) "Homotypic interactions and multimerization of the hepatitis C virus core protein" *Virology.*, 218:43-51 (Exhibit 19).
Matsumoto, M., et al. (1997) "Hepatitis C virus core protein interacts with the cytoplasmic tail of lymphotoxin-β receptor" *J. Virol.* 71:1301-1309 (Exhibit 20).
Moradpour, D., Kary, P., rice, C. M., and Blum, H.E. (1998) "Continuous human cell lines inducibly expressing hepatitis C virus structural and nonstructural proteins" *Hepatology*, 28:192-201 (Exhibit 21).
National Institutes of Health Consensus Development Conference Panel Statement (1997) "Management of Hepatitis C" *Hepatology*, 26:2S-10S (Exhibit 22).
Okamoto, H., et al. (1991) "Nucleotide sequence of the genomic RNA hepatitis C virus isolated from a human carrier: comparison with reported isolates from conserved and divergent regions" *J. Gen. Virol.*, 72:2697-6704 (Exhibit 23).
Ray, R. B., et al. (1996) "Hepatitis C virus core protein cooperates with ras and transforms primary rat embryo fibroblasts to tumorigenic phenotype" *J. Virol.*, 70:4438-4443 (Exhibit 24).

(Continued)

*Primary Examiner*—Laurie Scheiner
(74) *Attorney, Agent, or Firm*—John P. White, Esq.; Cooper & Dunham LLP

(57) ABSTRACT

The present invention provides a method of treating or preventing hepatitis C virus infection in a subject which comprises administering an effective amount of an agent to the subject, wherein the agent is capable of specifically binding to the HCV core protein so as to inhibit hepatitis C virus replication. The present invention also provides a method for determining whether a compound can treat or prevent hepatitis C virus infection in a subject, wherein the compound treats or prevents hepatitis C virus infection by specifically inhibiting the binding of HCV core protein and said agent so as to suppress hepatitis C virus replication. The present invention further provides a composition for inhibiting cell growth, comprises a HCV core protein or a variant thereof, wherein said HCV core protein or its variant inhibit cancer cell growth by inhibiting the cellular DEAD box proteins.

9 Claims, 12 Drawing Sheets

OTHER PUBLICATIONS

Ray, R. B., et al. (1997) "Transcriptional repression of p53 promoter by hepatitis C virus core protein" *J. Biol. Chem.*, 272:10983-10986 (Exhibit 25).

Reynolds, J. E., et al. (1995) "Unique features of internal initiation of hepatitis C virus RNA translation" *EMBO J.*, 14:6010-6020 (Exhibit 26).

Rozen, F., et al. (1990) "Bidirectional RNA helicase activity of eucaryotic translation initiation factors 4A and 4F" *Mol. Cell Biol.* 10:1134-1144 (Exhibit 27).

Selby, M. J., et al. (1993) "Expression, identification and subcellular localization of the proteins encoded by the hepatitis C viral genome" *J. Gen. Virol.*, 74:1103-1113 (Exhibit 28).

Suzuki, R., et al. "Nuclear localization of the truncated hepatitis C virus core protein with its hydrophobic C terminus deleted" *J. Gen. Virol.*, 76:53-61 (Exhibit 29).

Takamizawa, A., et al. (1991) "Structure and organization of the hepatitis C genome isolated from human carriers" *J. Viol.*, 65:1105-1113 (Exhibit 30).

Yao, N., et al. (1997) "Structure of the hepatitis C virus RNA helicase domain" *Nat. Struct. Biol.*, 4:63-467 (Exhibit 31).

Ye, Q., and Worman, H. J. (1996) "Interaction between an integral protein of the nuclear envelope inner membrane and human chromodomain proteins homologous to *Drosophila* HP1" *J. Biol. Chem.*, 271:14653-14656 (Exhibit 32).

Zhu, N., et al. (1998) "Hepatitis C virus core protein binds to cytoplasmic domain of tumor necrosis factor (TNF) receptor 1 and enhances TNF-induced apoptosis" *J. Virol.* 72:3691-3697 (Exhibit 33).

\* cited by examiner

FIGURE 2

SEQ. ID. NO: 1

MSHVAVENALGLDQQFAGLDLNSSDNQSGGSTASKGRYIPPHLRNREATRGFYDKDSSGWSSSKDKDAYSSFGSRSDSRGKSSFFS
DRGSGSRGRFDDRGRSDYDGIGSRGDRSGFGKFERGGNSRWCDKSDEDDWSKPLPPSERLEQELFSGGNTGINFEKYDDIPVEATG
NNCPPHIESFSDVEMGEIIMGNIELTRYTRPTPVQKHAIPIIKEKRDLMACAQTGSGKTAAFLLPILSQIYSDGPGEALRAMKENG
RYGRRKQYPISLVLAPTRELAVQIYEEARKFSYRSRVRPCVVYGGADIGQQIRDLERGCHLLVATPGRLVDMMERGKIGLDFCKYL
VLDEADRMLDMGFEPQIRRIVEQDTMPPKGVRHTMMFSATFPKEIQMLARDFLDEYIFLAVGRVGSTSENITQKVVWVEESDKRSF
LLDLLNATGKDSLTLVFVETKKGADSLEDFLYHEGYACTSIHGDRSQRDREEALHQFRSGKSPILVATAVAARGLDISNVKHVINF
DLPSDIEEYVHRIGRTGRVGNLGLATSFFNERNINITKDLLDLLVEAKQEVPSWLENMAYEHHYKGSSRGRSKSSSRFSGGFGARDY
RQSSGASSSSFSSSRASSSRSGGGHGSSRGFGGGYGGGFYNSDGYGGNYNSQGVDWWGN

SEQ. ID. NO: 2

GSTSENITQKVVWVEESDKRSFLLDLLNATGKDSLTLVFVETKKGADSLEDFLYHEGYACTSIHGDRSQRDREEALHQFRSGKSPI
LVATAVAARGLDISNVKHVINFDLPSDIEEYVHRIGRTGRVGNLGLATSFFNERNINITKDLLDLLVEAKQEVPSWLENMAYEHHY
KGSSRGRSKSSSRFSGGFGARDYRQSSGASSSSFSSSRASSSRSGGGHGSSRGFGGGYGGGFYNSDGYGGNYNSQGVDWWGN

FIGURE 3

SEQ. ID. NO:3

VGSTSENITQKVVWVEESDKRSFLLDLLNATGKDSLTLVFVETKKGADSLEDFLYHEGYACTSIHGDRSQRDREEALHQFRSGKSP
ILVATAVAARGLDISNVKHVINFDLPSDIEEYVHRIGRTGRVGNLGLAT

FIGURE 4

SEQ. ID. NO:4

```
  1 atggatgatc gagaggatct ggtgtaccag gcgaagctgg ccgagcaggc tgagcgatac
 61 gacgaaatgg tggagtcaat gaagaaagta gcagggatgg atgtggagct gacagttgaa
121 gaaagaaacc tcctatctgt tgcatataag aatgtgattg gagctagaag agcctcctgg
181 agaataatca gcagcattga acagaaagaa gaaaacaagg gaggagaaga caagctaaaa
241 atgattcggg aatatcggca atggttgagg actgagctaa agttaatctg ttgtgacatt
301 ctggatgtac tggacaaaca cctcattcca gcagctaaca ctggcgagtc caaggttttc
361 tattataaaa tgaaagggga ctaccacagg tatctggcag aatttgccac agaaacgac
421 aggaaggagg ctgcggagaa cagcctagtg gcttataaag ctgctagtga tattgcaatg
481 acagaacttc caccaacgca tcctattcgc ttaggtcttg ctctcaattt ttccgtattc
541 tactacgaaa ttcttaattc cctgaccgt gcctgcaggt tggcaaaagc agcttttgat
601 gatgcaattg cagaactgga tacgctgagt gaagaaagct ataaggactc tacacttatc
661 atgcagttgt tacgtgataa tctgacacta tggacttcag acatgcaggg tgacggtgaa
721 gagcagaata aagaagcgct gcaggacgtg gaagacgaaa atcagtgaga cataagccaa
781 caagagaaac ca
```

SEQ. ID. NO:5 translation="MDDREDLVYQAKLAEQAERYDEMVESMKKVAGMDVELTVEERNL
LSVAYKNVIGARRASWRIISSIEQKEENKGGEDKLKMIREYRQMVETELKLICCDILD
VLDKHLIPAANTGESKVFYYKMKGDYHRYLAEFATGNDRKEAAENSLVAYKAASDIAM
TELPPTHPIRLGLALNFSVFYYEILNSPDRACRLAKAAFDDAIAELDTLSEESYKDST
LIMQLLRDNLTLWTSDMQGDGEEQNKEALQDVEDENQ"

*HCV Core Protein-DBX Interaction*

```
DBX    1   MSHVAVENALGLDQQFAGLDINSSDNQSGGGSTASKGRYIPPHLRNREATKGFYDKDSSGWSSSKDKDAYSSFGSRSDSRG
PL10   1   MSHVAEEDELGLDQQJAGLDLTSRDSQSGGGSTASKGRYIPPHLRNREAAKAFYDKDGSRW..SKDKDAYSSFGSRSDTRA
Ded1p  1   ..........MAEISEQVQNLSINDNNENG..........YMPPHLR........GKPRSARNNSSNYNNN..GGYNGCRG

DBX    81  KSSFFSDR.GSGSRGRFDDRGRSDYDGTGSRGCDRSGFGKFERGCN..SRWCDKSDEDDWSKPLPPSERLEQELFSGGNTG
PL10   79  KSSFFSDRCGSGSRGRFDERGRSDYESVGSRGCRSGFGKFERGCN..SRWCDKADEDDWSKPLPPSERLEQELFSGGNTG
Ded1p  53  GGSFFSN...NRRGGYGNGCFFGGNNGGSRSNGRSGCRWIDCKHVPAPRNEKAEIAIFGVPEDPNFQ........SSC

DBX    158 INFEKYDDIPVEATGNNCPPHIESFSDVEMGEIIMGNIELTRYTRPTPVQKHAIPIIKEKRDLMACAQTGSGKTAAFLLP
PL10   157 INFEKYDDIPVEATGNNCPPHIESFSDVEMGEIIMGNIELTRYTRPTPVQKHAIPIIKEKRDLMACAQTGSGKTAAFLLP
Ded1p  120 INFDNYDDIPIPVDASCKDVPEPITEFISPPIEDGEEENIKLARELTPTPVQKYSVPIVANGRDLMACAQTGSGKTCFLFP

DBX    238 ILSQIYSDGPGEALRAMKENGRYGRRKQYPISLVLAPTRELAVQIYEEARKFSYRSRVRPCVVYGGADIGQIRDLERGC
PL10   237 ILSQIYTDGPGEALRAMKENGKYGRRKQYPISLVLAPTRELAVQIYEEARKFSYRSRVRPCVVYGGADIGQIRDLERGC
Ded1p  200 VLSESEKTGPS....PQPESCGSFYQRKAYPTAVIMAPTRELATQIFDEAKKFTYRSMVKACVVYGGSPIGNQRETERGC

DBX    318 HLLVATPGRLVDMERGKIGLDFCKYLVLDEADRMLDMGFEPQIRRIVEQDTMPPKGVRHTMMFSATFPKEIQMLARDFL
PL10   317 HLLVATPGRLVDMERGKIGLDFCKYLVLDEADRMLDMGFEPQIRRIVEQDTMPPKGVRHTMMFSATFPKEIQMLARDFL
Ded1p  277 DLLVATPGRLINDFERGKISLANVKYLVLDEADRMLDMGFEPQIRHIVEDCDMTPVGERQTMFSATFPADIQHLARDFL

DBX    398 DEYIFLAVGRVGSTSENITQKVVWVEESDKRSFLLDLLNATGKDSLTLVFVETKKGADSLEDFLYHEGYACTSIHGDRSQ
PL10   397 DEYIFLAVGRVGSTSENITQKVVWVWEEADKRSFLLDLLNATGKDSLILVFVETKKGADSLEDFLYHEGYACTSIHGDRSQ
Ded1p  357 SDYIFLISVGRVGSTSENITQKVLEYVENQDKKSALDDLLSA.STDGLTLIFVETKRMADQITDFLIMONFRATAIHGDRTQ

DBX    478 RDREEALHQFRSGKSPILVATAVAARGLDISNVKHVINFDLPSDIEEYVHRIGRTGRVGNLGLATSFFNERNINITKDLL
PL10   477 RDREEALHQFRSGKSPILVATAVAARGLDISNVKHVINFDLPSDIEEYVHRIGRTGRVGNLGLATSFFNERNINITKDLL
Ded1p  436 SERERALAAFRSGAATLVATAVAARGLDIPNVTHVINYDLPSDVDDYVHRIGRTGRAGNTGLATAFFNSENSNIMGLH

DBX    558 DLLVEAKQEVPSWLENMAYEHHYKGSSRGRSKSSRFSGGFGARDYRQSSGASSSFSSSRASSSRSGGCHGSSRGFGGG
PL10   557 DLLVEAKQEVPSWLENMAFEHHYKGGSRGRSK.SRFSGGFGARDYRQSSGASSSFSSCRASNSRSGGSHGSSRGFGGG
Ded1p  516 EILTEANQEVPSHLKDAMMS....APCSRSNSRRGGF.CRNNNRDYRKAGGASAGGWGSSRSRDNSFRGGS......GWGSD

DBX    638 GYGGFYNSDGYGGNYNSQGVDWWGN
PL10   636 SYGGFYNSDGYGGNYSQGVDWWGN
Ded1p  587 S......KSSGCNSGGSNNSSMW..
```

FIGURE 6A

FIGURE 6B
DBX     PL10     Ded1p
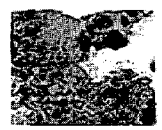 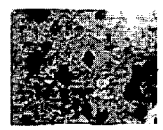

SEQUENCE LISTING

```
<160> NUMBER OF SEQ ID NOS: 6

<210> SEQ ID NO 1
<211> LENGTH: 666
<212> TYPE: PRT
<213> ORGANISM: Human

<400> SEQUENCE: 1
```

Met Ser His Val Ala Val Glu Asn Ala Leu Gly Leu Asp Gln Gln Phe
 1               5                  10                  15

Ala Gly Leu Asp Leu Asn Ser Ser Asp Asn Gln Ser Gly Gly Ser Thr
            20                  25                  30

Ala Ser Lys Gly Arg Tyr Ile Pro Pro His Leu Arg Asn Arg Glu Ala
        35                  40                  45

Thr Arg Gly Phe Tyr Asp Lys Asp Ser Ser Gly Trp Ser Ser Ser Lys
    50                  55                  60

Asp Lys Asp Ala Tyr Ser Ser Phe Gly Ser Arg Ser Asp Ser Arg Gly
65                  70                  75                  80

Lys Ser Ser Phe Phe Ser Asp Arg Gly Ser Gly Ser Arg Gly Arg Phe
                85                  90                  95

Phe Asp Asp Arg Gly Arg Ser Asp Tyr Asp Gly Ile Gly Ser Arg Gly
            100                 105                 110

Asp Arg Ser Gly Arg Gly Lys Phe Glu Arg Gly Gly Asn Ser Arg Trp
        115                 120                 125

Cys Asp Lys Ser Asp Glu Asp Asp Trp Ser Lys Pro Leu Pro Pro Ser
    130                 135                 140

Glu Arg Leu Glu Gln Glu Leu Phe Ser Gly Gly Asn Thr Gly Ile Asn
145                 150                 155                 160

Phe Glu Lys Tyr Asp Asp Ile Pro Val Glu Ala Thr Gly Asn Asn Cys
                165                 170                 175

Pro Pro His Ile Glu Ser Phe Ser Asp Val Val Val Glu Met Gly Glu
            180                 185                 190

Ile Ile Met Gly Asn Ile Glu Leu Thr Arg Tyr Thr Arg Pro Thr Pro
        195                 200                 205

Val Gln Lys His Ala Ile Pro Ile Ile Lys Glu Lys Arg Asp Leu Met
    210                 215                 220

-continued

```
Ala Cys Ala Gln Thr Gly Ser Gly Lys Thr Ala Ala Phe Leu Leu Pro
225                 230                 235                 240

Ile Leu Ser Gln Ile Tyr Ser Asp Gly Pro Gly Glu Ala Leu Arg Ala
                245                 250                 255

Met Lys Glu Asn Gly Arg Tyr Gly Arg Arg Lys Gln Tyr Pro Ile Ser
            260                 265                 270

Leu Val Leu Ala Pro Thr Arg Glu Leu Ala Val Gln Ile Tyr Glu Glu
        275                 280                 285

Ala Arg Lys Phe Ser Tyr Arg Ser Arg Val Arg Pro Cys Val Val Tyr
    290                 295                 300

Gly Gly Ala Asp Ile Gly Gln Gln Ile Arg Asp Leu Glu Arg Gly Cys
305                 310                 315                 320

His Leu Leu Val Ala Thr Pro Gly Arg Leu Val Asp Met Met Glu Arg
                325                 330                 335

Gly Lys Ile Gly Leu Asp Phe Cys Lys Tyr Leu Val Leu Asp Glu Ala
            340                 345                 350

Asp Arg Met Leu Asp Met Gly Phe Glu Pro Gln Ile Arg Arg Ile Val
        355                 360                 365

Glu Gln Asp Thr Met Pro Pro Lys Gly Val Arg His Thr Met Met Phe
    370                 375                 380

Ser Ala Thr Phe Pro Lys Glu Ile Gln Met Leu Ala Arg Asp Phe Leu
385                 390                 395                 400

Asp Glu Tyr Ile Phe Leu Ala Val Gly Arg Val Gly Ser Thr Ser Glu
                405                 410                 415

Asn Ile Thr Gln Lys Val Val Trp Val Glu Ser Asp Lys Arg Ser
            420                 425                 430

Phe Leu Leu Asp Leu Leu Asn Ala Thr Gly Lys Asp Ser Leu Thr Leu
        435                 440                 445

Val Phe Val Glu Thr Lys Lys Gly Ala Asp Ser Leu Glu Asp Phe Leu
    450                 455                 460

Tyr His Glu Gly Tyr Ala Cys Thr Ser Ile His Gly Asp Arg Ser Gln
465                 470                 475                 480

Arg Asp Arg Glu Glu Ala Leu His Gln Phe Arg Ser Gly Lys Ser Pro
                485                 490                 495

Ile Leu Val Ala Thr Ala Val Ala Ala Arg Gly Leu Asp Ile Ser Asn
            500                 505                 510

Val Lys His Val Ile Asn Phe Asp Leu Ser Pro Ser Asp Ile Glu Glu
        515                 520                 525

Tyr Val His Arg Ile Gly Arg Thr Gly Arg Val Gly Asn Leu Gly Leu
    530                 535                 540

Ala Thr Ser Phe Phe Asn Glu Arg Asn Ile Asn Ile Thr Lys Asp Leu
545                 550                 555                 560

Leu Asp Leu Leu Val Glu Ala Lys Gln Glu Val Pro Ser Trp Leu Glu
                565                 570                 575

Asn Met Ala Tyr Glu His His Tyr Lys Gly Ser Ser Arg Gly Arg Ser
            580                 585                 590

Lys Ser Ser Arg Phe Ser Gly Gly Phe Gly Ala Arg Asp Tyr Arg Gln
        595                 600                 605

Ser Ser Gly Ala Ser Ser Ser Phe Ser Ser Arg Ala Ser Ser
    610                 615                 620

Ser Arg Ser Gly Gly Gly Gly His Gly Ser Ser Arg Gly Phe Gly Gly
625                 630                 635                 640

Gly Gly Tyr Gly Gly Phe Tyr Asn Ser Asp Gly Tyr Gly Gly Asn Tyr
```

```
                        645                 650                 655
Asn Ser Gln Gly Val Asp Trp Trp Gly Asn
            660                 665

<210> SEQ ID NO 2
<211> LENGTH: 254
<212> TYPE: PRT
<213> ORGANISM: Human

<400> SEQUENCE: 2

Gly Ser Thr Ser Glu Asn Ile Thr Gln Lys Val Val Trp Val Glu Glu
  1               5                  10                  15

Ser Asp Lys Arg Ser Phe Leu Leu Asp Leu Leu Asn Ala Thr Gly Lys
             20                  25                  30

Asp Ser Leu Thr Leu Val Phe Val Glu Thr Lys Lys Gly Ala Asp Ser
         35                  40                  45

Leu Glu Asp Phe Leu Tyr His Glu Gly Tyr Ala Cys Thr Ser Ile His
     50                  55                  60

Gly Asp Arg Ser Gln Arg Asp Arg Glu Glu Ala Leu His Gln Phe Arg
 65                  70                  75                  80

Ser Gly Lys Ser Pro Ile Leu Val Ala Thr Ala Val Ala Ala Arg Gly
                 85                  90                  95

Leu Asp Ile Ser Asn Val Lys His Val Ile Asn Phe Asp Leu Pro Ser
            100                 105                 110

Asp Ile Glu Glu Tyr Val His Arg Ile Gly Arg Thr Gly Arg Val Gly
        115                 120                 125

Asn Leu Gly Leu Ala Thr Ser Phe Phe Asn Glu Arg Asn Ile Asn Ile
    130                 135                 140

Thr Lys Asp Leu Leu Asp Leu Leu Val Glu Ala Lys Gln Glu Val Pro
145                 150                 155                 160

Ser Trp Leu Glu Asn Met Ala Tyr Glu His His Tyr Lys Gly Ser Ser
                165                 170                 175

Arg Gly Arg Ser Lys Ser Ser Arg Phe Ser Gly Gly Phe Gly Ala Arg
            180                 185                 190

Asp Tyr Arg Gln Ser Ser Gly Ala Ser Ser Ser Phe Ser Ser Ser
        195                 200                 205

Arg Ala Ser Ser Ser Arg Ser Gly Gly Gly His Gly Ser Ser Arg
    210                 215                 220

Gly Phe Gly Gly Gly Tyr Gly Gly Phe Tyr Asn Ser Asp Gly Tyr
225                 230                 235                 240

Gly Gly Asn Tyr Asn Ser Gln Gly Val Asp Trp Trp Gly Asn
                245                 250

<210> SEQ ID NO 3
<211> LENGTH: 136
<212> TYPE: PRT
<213> ORGANISM: Human

<400> SEQUENCE: 3

Val Gly Ser Thr Ser Glu Asn Ile Thr Gln Lys Val Val Trp Val Glu
  1               5                  10                  15

Glu Ser Asp Lys Arg Ser Phe Leu Leu Asp Leu Leu Asn Ala Thr Gly
             20                  25                  30

Lys Asp Ser Leu Thr Leu Val Phe Val Glu Thr Lys Lys Gly Ala Asp
         35                  40                  45

Ser Leu Glu Asp Phe Leu Tyr His Glu Gly Tyr Ala Cys Thr Ser Ile
     50                  55                  60
```

```
                50              55              60
His Gly Asp Arg Ser Gln Arg Asp Arg Glu Ala Leu His Gln Phe
 65                      70                      75              80

Arg Ser Gly Lys Ser Pro Ile Leu Val Ala Thr Ala Val Ala Ala
                 85                      90                      95

Arg Gly Leu Asp Ile Ser Asn Val Lys His Val Ile Asn Phe Asp Leu
             100                     105                     110

Pro Ser Asp Ile Glu Glu Tyr Val His Arg Ile Gly Arg Thr Gly Arg
             115                     120                     125

Val Gly Asn Leu Gly Leu Ala Thr
             130                     135

<210> SEQ ID NO 4
<211> LENGTH: 792
<212> TYPE: DNA
<213> ORGANISM: Human
<220> FEATURE:
<221> NAME/KEY: CDS
<222> LOCATION: (1)..(765)

<400> SEQUENCE: 4
```

| | | | | | | | | | | | | | | | | |
|---|---|---|---|---|---|---|---|---|---|---|---|---|---|---|---|---|
| atg | gat | gat | cga | gag | gat | ctg | gtg | tac | cag | gcg | aag | ctg | gcc | gag | cag | 48 |
| Met | Asp | Asp | Arg | Glu | Asp | Leu | Val | Tyr | Gln | Ala | Lys | Leu | Ala | Glu | Gln | |
| 1 | | | | 5 | | | | | 10 | | | | | 15 | | |
| gct | gag | cga | tac | gac | gaa | atg | gtg | gag | tca | atg | aag | aaa | gta | gca | ggg | 96 |
| Ala | Glu | Arg | Tyr | Asp | Glu | Met | Val | Glu | Ser | Met | Lys | Lys | Val | Ala | Gly | |
| | | | 20 | | | | | 25 | | | | | 30 | | | |
| atg | gat | gtg | gag | ctg | aca | gtt | gaa | gaa | aga | aac | ctc | cta | tct | gtt | gca | 144 |
| Met | Asp | Val | Glu | Leu | Thr | Val | Glu | Glu | Arg | Asn | Leu | Leu | Ser | Val | Ala | |
| | | 35 | | | | | 40 | | | | | 45 | | | | |
| tat | aag | aat | gtg | att | gga | gct | aga | aga | gcc | tcc | tgg | aga | ata | atc | agc | 192 |
| Tyr | Lys | Asn | Val | Ile | Gly | Ala | Arg | Arg | Ala | Ser | Trp | Arg | Ile | Ile | Ser | |
| | 50 | | | | | 55 | | | | | 60 | | | | | |
| agc | att | gaa | cag | aaa | gaa | gaa | aac | aag | gga | gga | gaa | gac | aag | cta | aaa | 240 |
| Ser | Ile | Glu | Gln | Lys | Glu | Glu | Asn | Lys | Gly | Gly | Glu | Asp | Lys | Leu | Lys | |
| 65 | | | | | 70 | | | | | 75 | | | | | 80 | |
| atg | att | cgg | gaa | tat | cgg | caa | atg | gtt | gag | act | gag | cta | aag | tta | atc | 288 |
| Met | Ile | Arg | Glu | Tyr | Arg | Gln | Met | Val | Glu | Thr | Glu | Leu | Lys | Leu | Ile | |
| | | | | 85 | | | | | 90 | | | | | 95 | | |
| tgt | tgt | gac | att | ctg | gat | gta | ctg | gac | aaa | cac | ctc | att | cca | gca | gct | 336 |
| Cys | Cys | Asp | Ile | Leu | Asp | Val | Leu | Asp | Lys | His | Leu | Ile | Pro | Ala | Ala | |
| | | | 100 | | | | | 105 | | | | | 110 | | | |
| aac | act | ggc | gag | tcc | aag | gtt | ttc | tat | tat | aaa | atg | aaa | ggg | gac | tac | 384 |
| Asn | Thr | Gly | Glu | Ser | Lys | Val | Phe | Tyr | Tyr | Lys | Met | Lys | Gly | Asp | Tyr | |
| | | 115 | | | | | 120 | | | | | 125 | | | | |
| cac | agg | tat | ctg | gca | gaa | ttt | gcc | aca | gga | aac | gac | agg | aag | gag | gct | 432 |
| His | Arg | Tyr | Leu | Ala | Glu | Phe | Ala | Thr | Gly | Asn | Asp | Arg | Lys | Glu | Ala | |
| | 130 | | | | | 135 | | | | | 140 | | | | | |
| gcg | gag | aac | agc | cta | gtg | gct | tat | aaa | gct | gct | agt | gat | att | gca | atg | 480 |
| Ala | Glu | Asn | Ser | Leu | Val | Ala | Tyr | Lys | Ala | Ala | Ser | Asp | Ile | Ala | Met | |
| 145 | | | | | 150 | | | | | 155 | | | | | 160 | |
| aca | gaa | ctt | cca | cca | acg | cat | cct | att | cgc | tta | ggt | ctt | gct | ctc | aat | 528 |
| Thr | Glu | Leu | Pro | Pro | Thr | His | Pro | Ile | Arg | Leu | Gly | Leu | Ala | Leu | Asn | |
| | | | | 165 | | | | | 170 | | | | | 175 | | |
| ttt | tcc | gta | ttc | tac | tac | gaa | att | ctt | aat | tcc | cct | gac | cgt | gcc | tgc | 576 |
| Phe | Ser | Val | Phe | Tyr | Tyr | Glu | Ile | Leu | Asn | Ser | Pro | Asp | Arg | Ala | Cys | |
| | | | 180 | | | | | 185 | | | | | 190 | | | |
| agg | ttg | gca | aaa | gca | gct | ttt | gat | gat | gca | att | gca | gaa | ctg | gat | acg | 624 |
| Arg | Leu | Ala | Lys | Ala | Ala | Phe | Asp | Asp | Ala | Ile | Ala | Glu | Leu | Asp | Thr | |
| | | 195 | | | | | 200 | | | | | 205 | | | | |

```
ctg agt gaa gaa agc tat aag gac tct aca ctt atc atg cag ttg tta    672
Leu Ser Glu Glu Ser Tyr Lys Asp Ser Thr Leu Ile Met Gln Leu Leu
    210                 215                 220 cgt gat aat ctg aca cta tgg act tca gac atg cag ggt gac ggt gaa    720
Arg Asp Asn Leu Thr Leu Trp Thr Ser Asp Met Gln Gly Asp Gly Glu
225                 230                 235                 240 gag cag aat aaa gaa gcg ctg cag gac gtg gaa gac gaa aat cag        765
Glu Gln Asn Lys Glu Ala Leu Gln Asp Val Glu Asp Glu Asn Gln
                245                 250                 255 tgagacataa gccaacaaga gaaacca                                      792
```

<210> SEQ ID NO 5
<211> LENGTH: 255
<212> TYPE: PRT
<213> ORGANISM: Human

<400> SEQUENCE: 5

```
Met Asp Asp Arg Glu Asp Leu Val Tyr Gln Ala Lys Leu Ala Glu Gln
1               5                   10                  15

Ala Glu Arg Tyr Asp Glu Met Val Glu Ser Met Lys Lys Val Ala Gly
            20                  25                  30

Met Asp Val Glu Leu Thr Val Glu Glu Arg Asn Leu Leu Ser Val Ala
        35                  40                  45

Tyr Lys Asn Val Ile Gly Ala Arg Arg Ala Ser Trp Arg Ile Ile Ser
    50                  55                  60

Ser Ile Glu Gln Lys Glu Asn Lys Gly Gly Glu Asp Lys Leu Lys
65                  70                  75                  80

Met Ile Arg Glu Tyr Arg Gln Met Val Glu Thr Glu Leu Lys Leu Ile
                85                  90                  95

Cys Cys Asp Ile Leu Asp Val Leu Asp Lys His Leu Ile Pro Ala Ala
            100                 105                 110

Asn Thr Gly Glu Ser Lys Val Phe Tyr Lys Met Lys Gly Asp Tyr
        115                 120                 125

His Arg Tyr Leu Ala Glu Phe Ala Thr Gly Asn Asp Arg Lys Glu Ala
    130                 135                 140

Ala Glu Asn Ser Leu Val Ala Tyr Lys Ala Ala Ser Asp Ile Ala Met
145                 150                 155                 160

Thr Glu Leu Pro Pro Thr His Pro Ile Arg Leu Gly Leu Ala Leu Asn
                165                 170                 175

Phe Ser Val Phe Tyr Tyr Glu Ile Leu Asn Ser Pro Asp Arg Ala Cys
            180                 185                 190

Arg Leu Ala Lys Ala Ala Phe Asp Asp Ala Ile Ala Glu Leu Asp Thr
        195                 200                 205

Leu Ser Glu Glu Ser Tyr Lys Asp Ser Thr Leu Ile Met Gln Leu Leu
    210                 215                 220

Arg Asp Asn Leu Thr Leu Trp Thr Ser Asp Met Gln Gly Asp Gly Glu
225                 230                 235                 240

Glu Gln Asn Lys Glu Ala Leu Gln Asp Val Glu Asp Glu Asn Gln
                245                 250                 255
```

<210> SEQ ID NO 6
<211> LENGTH: 1928
<212> TYPE: PRT
<213> ORGANISM: Human

<400> SEQUENCE: 6

-continued

```
Met Ser His Val Ala Val Glu Asn Ala Leu Gly Leu Asp Gln Gln Phe
 1               5                  10                  15

Ala Gly Leu Asp Leu Asn Ser Ser Asp Asn Gln Ser Gly Gly Ser Thr
                 20                  25                  30

Ala Ser Lys Gly Arg Tyr Ile Pro Pro His Leu Arg Met Ser His Val
             35                  40                  45

Ala Glu Glu Asp Glu Leu Gly Leu Asp Gln Gln Leu Ala Gly Leu Asp
         50                  55                  60

Leu Thr Ser Arg Asp Ser Gln Ser Gly Gly Ser Thr Ala Ser Lys Gly
 65                  70                  75                  80

Arg Tyr Ile Pro Pro His Leu Arg Met Ala Glu Leu Ser Glu Gln Val
                 85                  90                  95

Gln Asn Leu Ser Ile Asn Asp Asn Asn Glu Asn Gly Tyr Val Pro Pro
                100                 105                 110

His Leu Arg Gly Lys Pro Arg Ser Ala Arg Asn Asn Ser Ser Asn Tyr
             115                 120                 125

Asn Asn Asn Asn Arg Glu Ala Thr Arg Gly Phe Tyr Asp Lys Asp
        130                 135                 140

Ser Ser Gly Trp Ser Ser Ser Lys Asp Lys Asp Ala Tyr Ser Ser Phe
145                 150                 155                 160

Gly Ser Arg Ser Asp Ser Arg Gly Lys Ser Ser Phe Ser Asp Arg
                165                 170                 175

Gly Ser Gly Ser Arg Gly Arg Phe Asp Asp Arg Gly Arg Ser Asn Arg
                180                 185                 190

Glu Ala Ala Lys Ala Phe Tyr Asp Lys Asp Gly Ser Arg Trp Ser Lys
            195                 200                 205

Asp Lys Asp Ala Tyr Ser Ser Phe Gly Ser Arg Ser Asp Thr Arg Ala
210                 215                 220

Lys Ser Ser Phe Phe Ser Asp Arg Gly Ser Gly Ser Arg Gly Arg
225                 230                 235                 240

Phe Asp Glu Arg Gly Arg Ser Asp Gly Tyr Asn Gly Gly Arg Gly
                245                 250                 255

Gly Gly Ser Phe Phe Ser Asn Asn Arg Gly Gly Tyr Gly Asn Gly
                260                 265                 270

Gly Phe Phe Gly Gly Asn Asn Gly Gly Ser Arg Ser Asn Gly Arg Ser
            275                 280                 285

Gly Gly Arg Trp Ile Asp Gly Lys His Val Pro Ala Pro Arg Asn Glu
        290                 295                 300

Lys Ala Asp Tyr Asp Gly Ile Gly Ser Arg Gly Asp Arg Ser Gly Phe
305                 310                 315                 320

Gly Lys Phe Glu Arg Gly Gly Asn Ser Arg Trp Cys Asp Lys Ser Asp
                325                 330                 335

Glu Asp Asp Trp Ser Lys Pro Leu Pro Pro Ser Glu Arg Leu Glu Gln
            340                 345                 350

Glu Leu Phe Ser Gly Gly Asn Thr Gly Ile Asn Phe Tyr Glu Ser Val
            355                 360                 365

Gly Ser Arg Gly Gly Arg Ser Gly Phe Gly Lys Phe Glu Arg Gly Gly
        370                 375                 380

Asn Ser Arg Trp Cys Asp Lys Ala Asp Glu Asp Asp Trp Ser Lys Pro
385                 390                 395                 400

Leu Pro Pro Ser Glu Arg Leu Glu Gln Glu Leu Phe Ser Gly Gly Asn
                405                 410                 415

Thr Gly Ile Asn Phe Glu Glu Ile Ala Ile Phe Gly Val Pro Glu Asp
```

-continued

```
                420             425             430
Pro Asn Phe Gln Ser Ser Gly Ile Asn Phe Asp Asn Tyr Asp Asp Ile
            435                 440                 445
Pro Val Asp Ala Ser Gly Lys Asp Val Pro Glu Pro Ile Thr Glu Phe
450                 455                 460
Thr Ser Pro Pro Leu Asp Gly Leu Leu Leu Glu Asn Ile Lys Leu Ala
465                 470                 475                 480
Glu Lys Tyr Asp Asp Ile Pro Val Glu Ala Thr Gly Asn Asn Cys Pro
                485                 490                 495
Pro His Ile Glu Ser Phe Ser Asp Val Glu Met Gly Glu Ile Ile Met
            500                 505                 510
Gly Asn Ile Glu Leu Thr Arg Tyr Thr Arg Pro Thr Pro Val Gln Lys
            515                 520                 525
His Ala Ile Pro Ile Ile Lys Glu Lys Arg Lys Tyr Asp Asp Ile Pro
            530                 535                 540
Val Glu Ala Thr Gly Asn Asn Cys Pro Pro His Ile Glu Ser Phe Ser
545                 550                 555                 560
Asp Val Glu Met Gly Glu Ile Ile Met Gly Asn Ile Glu Leu Thr Arg
                565                 570                 575
Tyr Thr Arg Pro Thr Pro Val Gln Lys His Ala Ile Pro Ile Ile Lys
            580                 585                 590
Glu Lys Arg Asp Arg Phe Thr Lys Pro Thr Pro Val Gln Lys Tyr Ser
            595                 600                 605
Val Pro Ile Val Ala Asn Gly Arg Asp Leu Met Ala Cys Ala Gln Thr
            610                 615                 620
Gly Ser Gly Lys Thr Gly Gly Phe Leu Phe Pro Val Leu Ser Glu Ser
625                 630                 635                 640
Phe Lys Thr Gly Pro Ser Pro Gln Pro Glu Ser Gln Gly Ser Asp Leu
                645                 650                 655
Met Ala Cys Ala Gln Thr Gly Ser Gly Lys Thr Ala Ala Phe Leu Leu
                660                 665                 670
Pro Ile Leu Ser Gln Ile Tyr Ser Asp Gly Pro Gly Glu Ala Leu Arg
            675                 680                 685
Ala Met Lys Glu Asn Gly Arg Tyr Gly Arg Arg Lys Gln Tyr Pro Ile
            690                 695                 700
Ser Leu Val Leu Ala Pro Thr Arg Leu Met Ala Ala Cys Ala Gln Thr
705                 710                 715                 720
Gly Ser Gly Lys Thr Ala Ala Phe Leu Leu Pro Ile Leu Ser Gln Ile
                725                 730                 735
Tyr Thr Asp Gly Pro Gly Glu Ala Leu Arg Ala Met Lys Glu Asn Gly
                740                 745                 750
Lys Tyr Gly Arg Arg Lys Gln Tyr Pro Ile Ser Leu Val Leu Ala Pro
            755                 760                 765
Thr Arg Glu Phe Tyr Gln Arg Lys Ala Tyr Pro Thr Ala Val Ile Met
            770                 775                 780
Ala Pro Thr Arg Glu Leu Ala Thr Gln Ile Phe Asp Glu Ala Lys Lys
785                 790                 795                 800
Glu Phe Thr Tyr Arg Ser Trp Val Lys Ala Cys Val Val Tyr Gly Gly
                805                 810                 815
Ser Pro Ile Gly Asn Gln Leu Arg Glu Ile Glu Arg Gly Cys Glu Leu
            820                 825                 830
Ala Val Gln Ile Tyr Glu Glu Ala Arg Lys Phe Ser Tyr Arg Ser Arg
            835                 840                 845
```

-continued

```
Val Arg Pro Cys Val Val Tyr Gly Gly Ala Asp Ile Gly Gln Gln Ile
850                 855                 860

Arg Asp Leu Glu Arg Gly Cys His Leu Leu Val Ala Thr Pro Gly Arg
865                 870                 875                 880

Leu Val Asp Met Met Glu Arg Gly Leu Ala Val Gln Ile Tyr Glu Glu
                885                 890                 895

Ala Arg Lys Phe Ser Tyr Arg Ser Arg Val Arg Pro Cys Val Val Tyr
            900                 905                 910

Gly Gly Ala Asp Ile Gly Gln Gln Ile Arg Asp Leu Glu Arg Gly Cys
                915                 920                 925

His Leu Leu Val Ala Thr Pro Gly Arg Leu Val Asp Met Met Glu Arg
930                 935                 940

Gly Lys Asp Leu Leu Val Ala Thr Pro Gly Arg Leu Asn Asp Leu Leu
945                 950                 955                 960

Glu Arg Gly Lys Ile Ser Leu Ala Asn Val Lys Tyr Leu Val Leu Asp
                965                 970                 975

Glu Ala Asp Arg Met Leu Asp Met Gly Phe Glu Pro Gln Ile Arg His
            980                 985                 990

Ile Val Glu Asp Cys Asp Met Thr Pro Val Gly Glu Lys Ile Gly Leu
        995                 1000                1005

Asp Phe Cys Lys Tyr Leu Val Leu Asp Glu Ala Asp Arg Met Leu Asp
    1010                1015                1020

Met Gly Phe Glu Pro Gln Ile Arg Arg Ile Val Glu Gln Asp Thr Met
1025                1030                1035                1040

Pro Pro Lys Gly Val Arg His Thr Met Met Phe Ser Ala Thr Phe Pro
                1045                1050                1055

Lys Glu Ile Gln Met Leu Ile Gly Leu Asp Phe Cys Lys Tyr Leu Val
            1060                1065                1070

Leu Asp Glu Ala Asp Arg Met Leu Asp Met Gly Phe Glu Pro Gln Ile
        1075                1080                1085

Arg Arg Ile Val Glu Gln Asp Thr Met Pro Pro Lys Gly Val Arg His
    1090                1095                1100

Thr Met Met Phe Ser Ala Thr Phe Pro Lys Glu Ile Gln Met Leu Ala
1105                1110                1115                1120

Arg Gln Thr Leu Met Phe Ser Ala Thr Phe Pro Ala Asp Ile Gln His
                1125                1130                1135

Leu Ala Arg Asp Phe Leu Ser Asp Tyr Ile Phe Leu Ser Val Gly Arg
            1140                1145                1150

Val Gly Ser Thr Ser Glu Asn Ile Thr Gln Lys Val Leu Tyr Val Glu
        1155                1160                1165

Asn Gln Asp Lys Lys Ser Ala Leu Leu Asp Ala Arg Asp Phe Leu Asp
    1170                1175                1180

Glu Tyr Ile Phe Leu Ala Val Gly Arg Val Gly Ser Thr Ser Glu Asn
1185                1190                1195                1200

Ile Thr Gln Lys Val Val Trp Val Glu Glu Ser Asp Lys Arg Ser Phe
                1205                1210                1215

Leu Leu Asp Leu Leu Asn Ala Thr Gly Lys Asp Ser Leu Thr Leu Val
            1220                1225                1230

Phe Val Glu Thr Arg Asp Phe Leu Asp Glu Tyr Ile Phe Leu Ala Val
        1235                1240                1245

Gly Arg Val Gly Ser Thr Ser Glu Asn Ile Thr Gln Lys Val Val Trp
    1250                1255                1260
```

-continued

```
Val Glu Glu Ala Asp Lys Arg Ser Phe Leu Leu Asp Leu Leu Asn Ala
1265                1270                1275                1280

Thr Gly Lys Asp Ser Leu Ile Leu Val Phe Val Thr Lys Leu Leu
            1285                1290                1295

Ser Ala Ser Thr Asp Gly Leu Thr Leu Ile Phe Val Glu Thr Lys Arg
            1300                1305                1310

Met Ala Asp Gln Leu Thr Asp Phe Leu Ile Met Gln Asn Phe Arg Ala
            1315                1320                1325

Thr Ala Ile His Gly Asp Arg Thr Gln Ser Glu Arg Glu Arg Ala Leu
            1330                1335                1340

Ala Ala Phe Arg Ser Gly Ala Ala Lys Lys Gly Ala Asp Ser Leu Glu
1345                1350                1355                1360

Asp Phe Leu Tyr His Glu Gly Tyr Ala Cys Thr Ser Ile His Gly Asp
            1365                1370                1375

Arg Ser Gln Arg Asp Arg Glu Glu Ala Leu His Gln Phe Arg Ser Gly
            1380                1385                1390

Lys Ser Pro Ile Leu Val Ala Thr Ala Val Ala Ala Arg Gly Leu Asp
            1395                1400                1405

Ile Ser Lys Gly Ala Asp Ser Leu Glu Asp Phe Leu Tyr His Glu Gly
    1410                1415                1420

Tyr Ala Cys Thr Ser Ile His Gly Asp Arg Ser Gln Arg Asp Arg Glu
1425                1430                1435                1440

Glu Ala Leu His Gln Phe Arg Ser Gly Lys Ser Pro Ile Leu Val Ala
            1445                1450                1455

Thr Ala Val Ala Ala Arg Gly Leu Asp Ile Ser Asn Thr Leu Leu Val
            1460                1465                1470

Ala Thr Ala Val Ala Ala Arg Gly Leu Asp Ile Pro Asn Val Thr His
            1475                1480                1485

Val Ile Asn Tyr Asp Leu Pro Ser Asp Val Asp Asp Tyr Val His Arg
    1490                1495                1500

Ile Gly Arg Thr Gly Arg Ala Gly Asn Thr Gly Leu Ala Thr Ala Phe
1505                1510                1515                1520

Glu Asn Ser Glu Asn Ser Asn Val Lys His Val Ile Asn Phe Asp Leu
            1525                1530                1535

Pro Ser Asp Ile Glu Glu Tyr Val His Arg Ile Gly Arg Thr Gly Arg
            1540                1545                1550

Val Gly Asn Leu Gly Leu Ala Thr Ser Phe Phe Asn Glu Arg Asn Ile
            1555                1560                1565

Asn Ile Thr Lys Asp Leu Leu Asp Leu Leu Val Glu Ala Lys Gln Glu
    1570                1575                1580

Val Lys His Val Ile Asn Phe Asp Leu Pro Ser Asp Ile Glu Glu Tyr
1585                1590                1595                1600

Val His Arg Ile Gly Arg Thr Gly Arg Val Gly Asn Leu Gly Leu Ala
            1605                1610                1615

Thr Ser Phe Phe Asn Glu Arg Asn Ile Asn Ile Thr Lys Asp Leu Leu
            1620                1625                1630

Asp Leu Leu Val Glu Ala Lys Gln Glu Val Asn Ile Val Lys Gly Leu
            1635                1640                1645

His Glu Ile Leu Thr Glu Ala Asn Gln Glu Val Pro Ser Phe Leu Lys
    1650                1655                1660

Asp Ala Met Met Ser Ala Pro Gly Ser Arg Ser Asn Ser Arg Arg Gly
1665                1670                1675                1680

Gly Phe Gly Arg Asn Asn Asn Arg Asp Tyr Arg Lys Ala Gly Gly Ala
```

-continued

```
                    1685                1690                1695
Ser Ala Gly Gly Val Pro Ser Trp Leu Glu Asn Met Ala Tyr Glu His
            1700                1705                1710
His Tyr Lys Gly Ser Ser Arg Gly Arg Ser Lys Ser Ser Arg Phe Ser
        1715                1720                1725
Gly Gly Phe Gly Ala Arg Asp Tyr Arg Gln Ser Ser Gly Ala Ser Ser
    1730                1735                1740
Ser Ser Phe Ser Ser Ser Arg Ala Ser Ser Ser Arg Ser Gly Pro Ser
1745                1750                1755                1760
Trp Leu Glu Asn Met Ala Phe Glu His His Tyr Lys Gly Gly Ser Arg
                1765                1770                1775
Gly Arg Ser Lys Ser Arg Phe Ser Gly Gly Phe Gly Ala Arg Asp Tyr
            1780                1785                1790
Arg Gln Ser Ser Gly Ala Ser Ser Ser Phe Ser Ser Gly Arg Ala
        1795                1800                1805
Ser Asn Ser Arg Ser Gly Gly Gly Trp Gly Ser Ser Arg Ser Arg Asp
    1810                1815                1820
Asn Ser Phe Arg Gly Gly Ser Gly Trp Gly Ser Asp Ser Lys Ser Ser
1825                1830                1835                1840
Gly Trp Gly Asn Ser Gly Gly Ser Asn Asn Ser Ser Trp Trp Gly Gly
                1845                1850                1855
Gly His Gly Ser Ser Arg Gly Arg Gly Gly Gly Gly Tyr Gly Gly Phe
            1860                1865                1870
Tyr Asn Ser Asp Gly Tyr Gly Gly Asn Tyr Asn Ser Gln Gly Val Asp
        1875                1880                1885
Trp Trp Gly Asn Ser His Gly Ser Ser Arg Gly Phe Gly Gly Gly Ser
    1890                1895                1900
Tyr Gly Gly Phe Tyr Asn Ser Asp Gly Tyr Gly Gly Asn Tyr Ser Ser
1905                1910                1915                1920
Gln Gly Val Asp Trp Trp Gly Asn
            1925
```

HCV CORE PROTEIN BINDING AGENTS FOR TREATMENT OF HEPATITIS C VIRUS INFECTION

Throughout this application, various publications are referenced by author and date. Full citations for these publications may be found listed numerically at the end of the specification immediately preceding the claims. The disclosures of these publications in their entireties are hereby incorporated by reference into this application in order to more fully describe the state of the art as known to those skilled therein as of the date of the invention described and claimed herein.

BACKGROUND OF THE INVENTION

Chronic hepatitis C is a major public health problem and one of the leading worldwide causes of chronic liver disease, cirrhosis and hepatocellular carcinoma (1). Approximately 4 million Americans are chronically infected with HCV and as many as 25% of them may eventually develop cirrhosis (2). End-stage liver disease from hepatitis C is now the leading indication for orthotopic liver transplantation in the United States. HCV was identified in 1989 and demonstrated to be the major cause of what was then referred to as non-A, non-B hepatitis (3, 4).

The hepatitis C virus (HCV) is a positive single stranded RNA virus and a member of the Flavivaridae family (3, 6–10). Once hepatitis C virus infects cells, the positive, single-stranded RNA genome is translated into a polyprotein of 3010 to 3033 amino acids, depending upon the strain (6–9). The viral RNA is not capped and translation occurs via internal ribosome entry sites (10, 11). The mechanism of translation from uncapped viral RNA therefore differs from that used by virtually all cellular mRNAs which are capped at their 5' ends.

In hepatocytes, the HCV core protein is mostly localized to endoplasmic reticulum membrane with a large domain facing the cytoplasm (12). It has been shown to form multimers (13). The function of HCV core protein in cells is not clear, however, it may play a role in transformation and oncogenesis (14). Such a function could hypothetically arise as a result of interactions with cellular proteins involved in signal transduction or oncogene or tumor suppressor gene products or by affecting expression from their genes. HCV core protein may also be involved in regulating the immune response as it has been shown to bind to the cytoplasmic domain of lymphotoxin-βreceptor (15). Some investigators have also shown that a truncated portion of HCV core protein can reach the nucleus (16, 17), suggesting that it may directly affect the expression of cellular genes as demonstrated in vitro (18). It is not clear, however, if this nuclear form is generated in infected cells.

The HCV polyprotein is proteolytically processed by both host cell and viral proteases into several smaller polypeptides (6–9, 12) (FIG. 1). The major structural proteins are a core protein and two envelope proteins (E1 and E2). Four major non-structural proteins called NS2, NS3, NS4, and NS5, are also generated, two of which, NS4 and NS5, are further processed into smaller polypeptides called NS4A, NS4B, NS5A, and NS5B. The non-structural proteins have various enzymatic activities, such as RNA helicase (NS3), protease (NS2, NS3–NS4A complex) and RNA polymerase (NS5B). NS5A has been implicated in determining sensitivity to interferon.

After cells are infected with a virus, viral proteins can interact with host cell proteins and influence cell physiology. In previous studies, HCV core protein has been shown to bind to lymphotoxin-β receptor and other tumor necrosis factor receptor family members (15, 27). A truncated form of HCV core protein also interacts with ribonucleoprotein K in the nucleus (28). We now show that HCV core protein binds to a cellular RNA helicase and, in experimental systems, inhibits capped RNA translation. This provides a novel mechanism by which HCV may inhibit mRNA translation in infected cells or recruit a cellular protein to enhance its own replication.

Despite major advances in diagnosing chronic hepatitis C and screening the blood supply since that time, almost nothing is known about how the virus infects, kills or transforms cells. For this reason, current therapeutic options are limited and new agents have been difficult to develop.

According to a recent National Institutes of Health Consensus Development Conference Panel Statement on the Management of Hepatitis C (5), there is an urgent need for effective antiviral therapeutics capable of inhibiting HCV replication and stopping or delaying the progression of liver disease. The Panel also concluded that a major bottleneck to the drug discovery process is the absence of a readily available cell culture system that is fully permissive for viral replication. A small animal model of HCV infection is also lacking. For these reasons, novel, alternative approaches must be developed to identify targets for the design of therapeutic agents for the treatment of patients with chronic hepatitis C.

The development of specific drugs against HCV has been impeded because there is no non-primate animal model of infection and all attempts to culture the virus have failed. Currently, the only currently approved drugs in the United States are preparations of interferon-alpha and ribavirin. The long-term cure rate of subjects treated with interferon-alpha is less than 10%. The use of ribavirin, in combination with interferon-alpha, has shown slightly better long-term cure, however, still in only a minority of subjects.

SUMMARY OF THE INVENTION

The present invention provides a method of treating or preventing hepatitis C virus infection in a subject which comprises administering an effective amount of an agent to the subject, wherein the agent is capable of specifically binding to the HCV core protein so as to inhibit hepatitis C virus replication. The present invention provides a method of identifying a compound which can inhibit the functions of hepatitis C virus, wherein said compound inhibits hepatitis C virus replication by inhibiting the interactions between HCV core protein and an agent capable of specifically binding to said HCV core protein, comprising: (a) incubating said compound, the HCV core protein and said agent under a suitable reaction conditions, (b) determining the binding between the HCV core protein and said agent in the presence of said compound, and (c) comparing the binding in step (b) with the binding between the HCV core protein and said agent in the absence of said compound so as to identify a compound which can inhibit the replication of hepatitis C virus by inhibiting the binding between HCV core protein and said agent.

The present invention also provides a method for determining whether a compound can treat or prevent hepatitis C virus infection in a subject, comprising (a) incubating said compound, the HCV core protein and an agent capable of specifically binding to said HCV core protein, (b) determining the binding between the HCV core protein and said agent in the presence of said compound, and (c) comparing the binding in step (b) with the binding between the HCV core protein and said agent in the absence of said compound so as to identify a compound which can treat or prevent hepatitis C virus infection in a subject, wherein said compound treats or prevents hepatitis C virus infection by specifically inhibiting the binding of HCV core protein and said agent so as to suppress hepatitis C virus replication.

The present invention further provides a composition for inhibiting cell growth, comprises a HCV core protein or a variant thereof, wherein said HCV core protein or its variant inhibit cancer cell growth by inhibiting the cellular DEAD box proteins.

BRIEF DESCRIPTION OF THE FIGURES

FIG. 2: Amino acid sequence of human DBX (alternative transcript 2), SEQ ID NO:1. The domain that binds to HCV core protein in the yeast two-hybrid assay is underlined and separately listed as SEQ ID NO:2.

FIG. 3: Amino acid sequence of human DBX (alternative transcript 2) from amino acid 509 to amino acid 645 (SEQ ID NO:3) that binds to HCV core protein in the yeast two hybrid assay.

FIG. 4: Complete cDNA sequence of human epsilon 14-3-3 protein (SEQ ID NO:4) and amino acid sequence translation thereof (SEQ ID NO:5).

Figure 1:
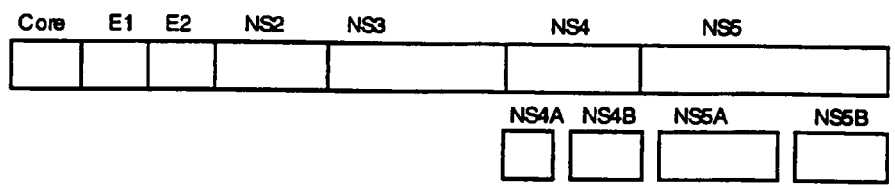
FIG. 1: Diagram of the major processed proteins encoded by the HCV genome. The 3010–3033 amino acid polyprotein is processed into several smaller polypeptides. Core, E1 and E2 are structural polypeptides. Core protein is the virus nucleocapsid and E1 and E2 are viral envelope proteins. The major non-structural proteins are NS2, NS3, NS4 and NS5. NS4 is further processed into NS4A and NS4B and NS5 into NS5A and NS5B. NS2 and part of NS3 are proteases that process the viral polyprotein. NS3 also has RNA-helicase activity. NS4A is a cofactor for the NS3 protease and NS5B is an RNA-dependent, RNA polymerase. The functions of NS4B and NS5A are less-well understood but NS5A is thought to play a role in determining sensitivity to interferon.

5A: A standard amount of $^{35}$S-HCV core protein (amino acids 1–123), 10% of which is shown in the autoradiogram (lane 1), was used in each binding assay. $^{35}$S-HCV core protein was incubated with glutathione-Sepharose (lane 2), 20 μg of GST coupled to glutathione-Sepharose (lane 3) in binding buffer containing 0.15 M NaCl and 0.2 μg of GST-DBX fusion protein coupled to glutathione-Sepharose in buffers containing the NaCl concentrations indicated above each lane (lanes 4–8). Glutathione-Sepharose was then washed with buffer containing the indicated NaCl concentration and the bound proteins were eluted with 4% SDS, subjected to SDS-polyacrylamide gel electrophoresis and detected by autoradiography of dried slabs gels.

5B: Binding assay similar to that shown in panel A in which GST-DBX fusion protein was incubated with $^{35}$S-HCV core protein in buffers containing 0.15 M NaCl and 0.05% to 1.0% of Nonidet P-40 (NP-40) (lanes 4–6). Migrations of molecular mass standards are indicated in kilodaltons at the left of each panel.

FIG. 6: Primary structures of DBX, PL10 and Ded1 and their interactions with HCV core protein in the yeast two-hybrid assay.

6A: Alignment of deduced amino acid sequences of DBX (GenBank Accession number AF000982), PL10 (GenBank Accession number J04847) and Ded1p (GenBank Accession number X57278) is shown. Identical amino acids are shown as white on black. Conserved substitutions are shown as black on gray. Dots represent gaps to optimize alignments which were obtained using the Pileup program.

6B: Two-hybrid assays showing interaction of HCV core protein with DBX and PL10 but not with Ded1p. Yeast strain Y190 was co-transformed with a plasmid expressing the cytoplasmic domain of HCV fused to the GAL4 DNA binding domain and plasmids expressing either a portion of DBX or the corresponding portions of PL10 or Ded1p fused to the GAL4 transcriptional activation domain. Transformants giving β-galactosidase activity (positive interactions) are blue. Control reactions of DBX, PL10 and Dep1p GAL 4 activation domain fusion proteins with GAL4 DNA binding domain alone were negative (data not shown).

FIG. 7: Immunofluorescence localization of DBX and HCV core protein in mammalian cells.

7A: Hela cells were transiently transfected with cDNA encoding FLAG-tagged HCV core protein (left panel) or with cDNA encoding myc-tagged DBX (right panel). Cells were incubated with monoclonal anti-FLAG or anti-myc (9E10) antibody followed by rhodamine-conjugated secondary antibody. HCV core protein appears primarily in large, discrete foci at the endoplasmic reticulum membrane whereas DBX has a more diffuse cytoplasmic localization.

7B: Co-localization of DBX and HCV core protein in COS-7 cells transiently transfected to express both FLAG-tagged HCV core protein and myc-tagged DBX. All cells were fixed and incubated with the same combination of rabbit anti-FLAG polyclonal antibody and mouse anti-myc monoclonal (9E10) antibody followed by both fluorescein isothiocyante-conjugated goat anti-rabbit and rhodamine-conjugated goat anti-mouse antibodies. Cells transfected to express FLAG-tagged HCV core protein alone (left column) showed essentially only green fluorescence resulting from anti-FLAG and fluorescein isothiocyanate-conjugated antibody labeling (row G). Cells transfected to express myc-tagged DBX alone (middle column) showed essentially only red fluorescence resulting from anti-myc and rhodamine conjugated antibody labeling (row R). The right column shows COS-7 cells co-transfected to express both FLAG-tagged HCV core protein (row G) and myc-tagged DBX (row R). Merged images (row M) appear yellow where green fluorescence corresponding to HCV core protein localization and red fluorescence corresponding to DBX localization overlap.

Figure 8:
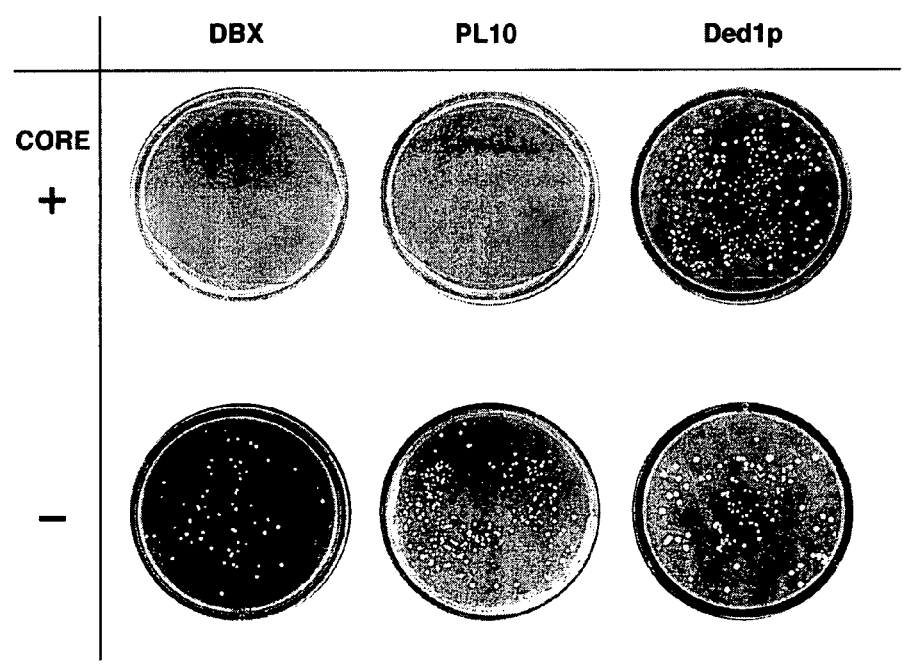

FIG. 8: Inhibition of DBX and PL10 but not Ded1p by HCV core protein. Yeast strains with chromosomal ded1 deletion complemented with either DBX, PL10, or DED1 cDNAs driven by the yeast GPD promoter on centromeric plasmids were transformed with a plasmid that expressed full-length HCV core protein (top) or control plasmid p423GPD (bottom). The resulting transformants were spread on histidine, leucine drop-out plates and incubated at 30° C. for 7 days and photographs (negatives are shown) were taken of each plate. Note colony growth of all yeast strains transfected with control plasmid (bottom panels). In contrast, DBX- and PL10-complemented ded1-deletion strains do not demonstrate significant colony growth when HCV core protein is expressed whereas growth of the DED1-complemented strain is unaffected (top panels).

Figure 9:
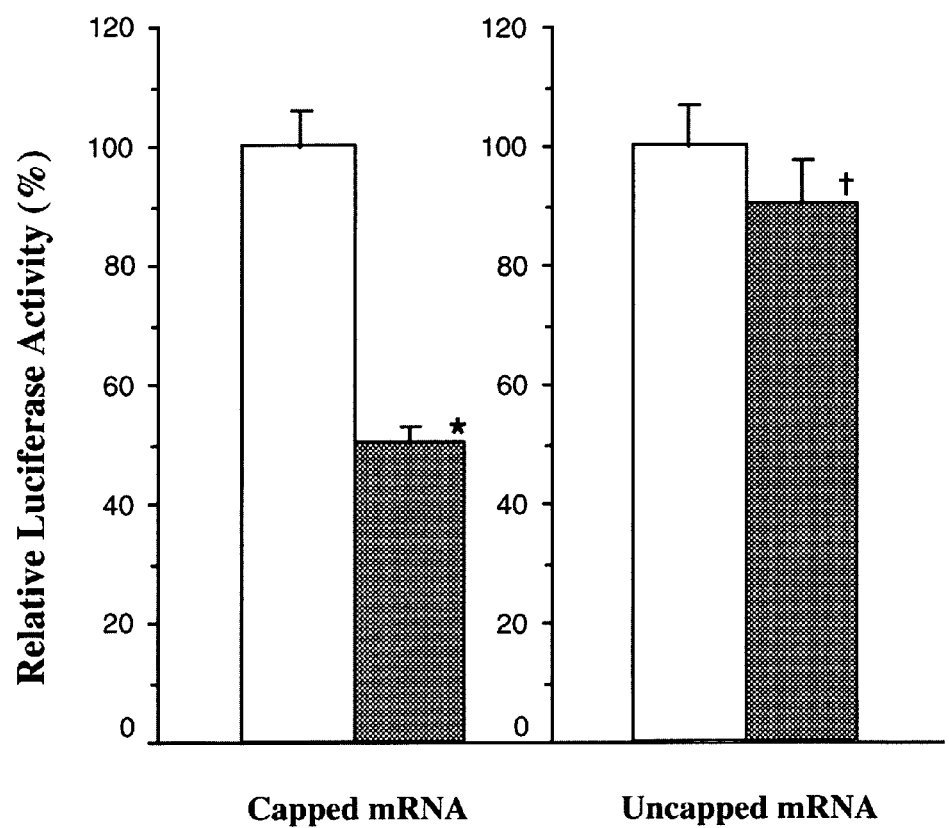

FIG. 9: Inhibition of translation of capped mRNA in vitro by HCV core protein. Rabbit reticulocyte lysates were incubated with glutathione-Sepharose beads loaded with either 300 ng of a GST-HCV core fusion protein or GST. In vitro synthesized capped or non-capped luciferase mRNAs were translated at 30° C. for 90 minutes and luciferase activity was measured. Results are expressed as the relative luciferase activities produced in reticulocyte lysates treated equal concentrations of GST-HCV core fusion protein (shaded bars) or GST (open bars, arbitrarily assigned 100% activity). Values shown are means±standard errors (n=6). *p<0.0001: no significant difference.

DETAILED DESCRIPTION OF THE INVENTION

The present invention provides a method of treating or preventing hepatitis C virus infection in a subject which comprises administering an effective amount of an agent to the subject, wherein the agent is capable of specifically binding to the HCV core protein so as to inhibit hepatitis C virus replication.

In one embodiment of the method, the agent is capable of specifically binding to the HCV core protein having an amino acid sequence of FIG. 2, SEQ ID NO:1.

As used herein, "inhibition of hepatitis C virus replication" means interrupting or stopping the growth or multiplication of the hepatitis C virus.

In another embodiment of the method, the binding of the agent to hepatitis C virus core protein prevents the hepatitis C virus from attaching to the cells of the subject so as to inhibit hepatitis C virus replication.

In another embodiment of the method, the binding of the agent to hepatitis C virus core protein prevents the hepatitis C virus from entering into the cells of the subject so as to inhibit hepatitis C virus replication.

In another embodiment of the method, the agent binds to the cytoplasmic domain of HCV core protein which comprises amino acid residues 1–123 of said HCV core protein of FIG. 2, SEQ ID NO:1.

In another embodiment of the method, the agent is a polypeptide, a pseudo enzyme, a peptidomimetic compound, a nucleic acid molecule, an antibody or variant thereof.

In another embodiment of the method, the agent comprises a cellular protein.

In another embodiment of the method, the cellular protein comprises a DEAD-box protein, or a 14-3-3 protein.

In another embodiment of the method, the DEAD box protein comprises a DEAD box RNA helicase.

In another embodiment of the method, the DEAD-box RNA helicase is a human DEAD-box protein DBX or a variant thereof.

Variants in amino acid sequence of human DEAD-box protein DBX are produced when one or more amino acids in naturally occurring human DEAD-box protein DBX is substituted with a different natural amino acid, an amino acid derivative, a synthetic amino acid, an amino acid analog or a non-native amino acid. Particularly preferred variants include homologous human DEAD-box protein DBX. Variants of a human DEAD-box protein DBX may include biologically active fragments of naturally occurring human DEAD-box protein DBX, wherein sequences of the variant differ from the wild type human DEAD-box protein DBX sequence by one or more conservative amino acid substitutions. Such substitutions typically would have minimal influence on the secondary structure and hydrophobicity of human DEAD-box protein DBX.

In another embodiment of the method, the human DEAD-box protein DBX has the amino acid sequence of FIG. 2, SEQ ID NO:1.

"Polypeptide" includes both peptides and proteins. "Peptide" means a polypeptide of fewer than 10 amino acid residues in length, and "protein" means a polypeptide of 10 or more amino acid residues in length. In this invention, the polypeptides may be naturally occurring or recombinant (i.e. produced via recombinant DNA technology), and may contain mutations (e.g. point, insertion and deletion mutations) as well as other covalent modifications (e.g. glycosylation and labeling via biotin, streptavidin, fluoracine, and radioisotopes such as $^{131}$I). Moreover, each instant composition may contain more than a single polypeptide, i.e. each may be a monomer (one polypeptide bound to a polymer) or a multimer (two or more polypeptides bound to a polymer or to each other).

As used herein, "effective amount" means an amount of a compound which interrupts the binding between hepatitis C virus core protein and a cellular protein, which can inhibit the hepatitis C virus replication and can be determined using methods well known to those skilled in the art.

In another embodiment of the method, the variant of human DEAD-box protein DBX comprises the amino acid sequence of FIG. 2, SEQ ID NO:2.

In another embodiment of the method, the variant of human DEAD-box protein DBX comprises the amino acid sequence of FIG. 3, SEQ ID NO:3.

In another embodiment of the method, the hepatitis C virus infects the liver of the subject.

In another embodiment of the method, the hepatitis C virus infects the liver of a human.

In another embodiment of the method, the variant of the human DEAD-box protein DBX comprises 100–200 amino acid residues which mimics the amino acid sequence of FIG. 2, SEQ ID NO:2 or the amino acid sequence of FIG. 3, SEQ ID NO: 3.

In another embodiment of the method, the 14-3-3 protein comprises the amino acid sequence of FIG. 4, SEQ ID NO:5 or a variant thereof.

Variants in amino acid sequence of 14-3-3 protein are produced when one or more amino acids in naturally occurring 14-3-3 protein is substituted with a different natural amino acid, an amino acid derivative, a synthetic amino acid, an amino acid analog or a non-native amino acid. Particularly preferred variants include homologous 14-3-3 protein. Variants of a 14-3-3 protein may include biologically active fragments of naturally occurring 14-3-3 protein, wherein sequences of the variant differ from the wild type 14-3-3 protein sequence by one or more conservative amino acid substitutions. Such substitutions typically would have minimal influence on the secondary structure and hydrophobicity of the 14-3-3 protein.

In another embodiment of the method, the variant of said 14-3-3 protein comprises 50–200 amino acid residues which mimics the active site of said 14-3-3 protein of FIG. 4, SEQ ID NO:5.

In another embodiment of the method, the agent comprises nucleic acid molecule encoding DEAD-box protein of FIG. 4, SEQ ID NO:5 or a variant thereof.

In yet another embodiment of the method, the agent comprises nucleic acid molecule encoding 14-3-3 protein of FIG. 4, SEQ ID NO:5 or a variant thereof.

In a further embodiment of the method, the agent is administered with a pharmaceutically acceptable carrier.

The present invention provides a method of identifying a compound which can inhibit the replication of HCV, wherein said compound inhibits hepatitis C virus replication by inhibiting the binding between HCV core protein and an agent capable of specifically binding to said HCV core protein, comprising: (a) incubating said compound, the HCV core protein and said agent under a suitable reaction conditions, (b) measuring the binding between the HCV core protein and said agent in the presence of said compound, and (c) comparing the binding in step (b) with the binding between the HCV core protein and said agent in the absence of said compound so as to identify a compound which can inhibit the replication of hepatitis C virus by inhibiting binding between HCV core protein and said agent.

In one embodiment of the method, the agent is known to bind to HCV core protein.

In another embodiment of the method, the binding of the agent to hepatitis C virus core protein prevents the hepatitis C virus from attaching to the cells of the subject so as to inhibit hepatitis C virus replication.

In another embodiment of the method, the binding of the agent to hepatitis C virus core protein prevents the hepatitis C virus from entering into the cells of the subject so as to inhibit hepatitis C virus replication.

In another embodiment of the method, the inhibition of HCV replication is in a subject.

In another embodiment of the method, the agent is a polypeptide, a pseudo enzyme, a peptidomimetic compound, a nucleic acid molecule, an antibody or variant thereof.

In another embodiment of the method, the agent comprises a cellular protein.

In another embodiment of the method, the cellular protein comprises a DEAD-box protein, or a 14-3-3 protein.

In another embodiment of the method, the DEAD box protein comprises a DEAD box RNA helicase.

In another embodiment of the method, the DEAD-box RNA helicase comprises a human DEAD-box protein DBX or a variant thereof.

In another embodiment of the method, the human DEAD-box protein DBX comprises the amino acid sequence of FIG. 2 SEQ ID NO:1.

In another embodiment of the method, the variant of the human DEAD-box protein DBX comprises the amino acid sequence of FIG. 2, SEQ ID NO:2.

In another embodiment of the method, the variant of the human DEAD-box protein DBX comprises the amino acid sequence of FIG. 3, SEQ ID NO:3.

In another embodiment of the method, the variant of the human DEAD-box protein DBX comprises 100–200 amino acid residues which mimics the amino acid sequence of FIG. 2, SEQ ID NO:2 or the amino acid sequence of FIG. 3, SEQ ID NO:3.

In another embodiment of the method, the 14-3-3 protein comprises the amino acid sequence of FIG. 4, SEQ. ID NO:5 or a variant thereof.

In another embodiment of the method, the variant of said 14-3-3 protein comprises 50–200 amino acid residues which mimics the active site of said 14-3-3 protein of FIG. 4, SEQ ID NO:5.

In another embodiment of the method, the agent comprises nucleic acid molecule encoding DEAD-box protein of FIG. 2, SEQ ID NO:1 or a variant thereof.

In another embodiment of the method, the agent comprises nucleic acid molecule encoding 14-3-3 protein of FIG. 4, SEQ ID NO:5 or a variant thereof.

In another embodiment of the method, the agent comprises administered with a pharmaceutically acceptable carrier.

In another embodiment of the method, the inhibition of hepatitis C virus replication is in vitro.

In another embodiment of the method, the subject is a mammal.

In another embodiment of the method, the subject is a human.

In another embodiment of the method, the inhibition of hepatitis C virus replication occurs in the liver of the subject.

In another embodiment of the method, the inhibition of hepatitis C virus replication occurs in the liver of a human.

In another embodiment of the method, the binding between the HCV core protein and the agent is measured by yeast two-hybrid screening.

In yet another embodiment of the method, the compound is not previously known.

In a further embodiment of the method, the previously unknown compound is identified by the method.

The present invention also provides a composition comprising an effective amount of the compound identified by the method which is capable of inhibiting the binding between hepatitis C virus core protein and a cellular protein.

The present invention also provides a pharmaceutical composition comprising an effective amount of the compound identified by the method which is capable of treating or preventing hepatitis C virus infection.

The present invention also provides a method for determining whether a compound can treat or prevent hepatitis C virus infection in a subject, comprising (a) incubating said compound, the HCV core protein and an agent capable of specifically binding to said HCV core protein, (b) determining the binding between the HCV core protein and said agent in the presence of said compound, and (c) comparing the binding in step (b) with the binding between the HCV core protein and said agent in the absence of said compound so as to identify a compound which can treat or prevent hepatitis C virus infection in a subject, wherein said compound treats or prevents hepatitis C virus infection by specifically inhibiting the binding of HCV core protein and said agent so as to suppress hepatitis C virus replication.

In one embodiment of the method, the agent is known to bind to HCV core protein.

In another embodiment of the method, the binding of the agent to hepatitis C virus core protein prevents the hepatitis C virus from attaching to the cells of the subject so as to treat or prevent hepatitis C virus infection.

In another embodiment of the method, the binding of the agent to hepatitis C virus core protein prevents the hepatitis C virus from entering into the cells of the subject so as to treat or prevent hepatitis C virus infection.

In another embodiment of the method, the subject is a mammal.

In another embodiment of the method, the subject is a human.

In another embodiment of the method, the hepatitis C virus replication occurs in the liver of the subject.

In another embodiment of the method, the hepatitis C virus replication occurs in the liver of a human.

In another embodiment of the method, the compound can be administered orally or by injection.

In another embodiment of the method, the compound is not previously known.

In another embodiment of the method, the previously unknown compound is identified by said method.

In another embodiment of the method, the agent is a polypeptide, a pseudo enzyme, a peptidomimetic, a nucleic acid, an antibody or variant thereof.

In another embodiment of the method, the agent comprises a cellular protein.

In another embodiment of the method, the cellular protein comprises a DEAD-box protein, or a 14-3-3 protein.

In another embodiment of the method, the DEAD box protein comprises a DEAD box RNA helicase.

In another embodiment of the method, the DEAD-box RNA helicase comprises a human DEAD-box protein DBX or a variant thereof.

In another embodiment of the method, the human DEAD-box protein DBX comprises the amino acid sequence of FIG. 2 SEQ ID NO:1.

In another embodiment of the method, the variant of the human DEAD-box protein DBX comprises the amino acid sequence of FIG. 2, SEQ ID NO:2.

In another embodiment of the method, the variant of the human DEAD-box protein DBX comprises the amino acid sequence of FIG. 3, SEQ ID NO:3.

In another embodiment of the method, the variant of the human DEAD-box protein DBX comprises 100–200 amino acid residues which mimics the amino acid sequence of FIG. 2, SEQ ID NO:2 or the amino acid sequence of FIG. 3, SEQ ID NO:3.

In another embodiment of the method, the 14-3-3 protein comprises the amino acid sequence of FIG. 4, SEQ ID NO:5 or a variant thereof.

In another embodiment of the method, the variant of said 14-3-3 protein comprises 50–200 amino acid residues which mimics the active site of said 14-3-3 protein, FIG. 4, SEQ ID NO:5.

In another embodiment of the method, the agent comprises nucleic acid molecule encoding DEAD-box protein of FIG. 2, SEQ ID NO:1 or a variant thereof.

In yet another embodiment of the method, the agent comprises nucleic acid molecule encoding 14-3-3 protein of FIG. 4, SEQ ID NO:5 or a variant thereof.

In a further embodiment of the method, the agent comprises administered with a pharmaceutically acceptable carrier.

The present invention further provides a composition for inhibiting cell growth, comprises a HCV co re protein or a variant thereof, wherein said HCV core protein or its variant inhibit cancer cell growth by inhibiting the cellular DEAD box proteins.

In one embodiment of the composition, the growth of cancer cells are inhibited.

As used herein, "subject" means any animal, including, for example, mice, rats, dogs, guinea pigs, ferrets, rabbits, and primates. In the preferred embodiment, the subject is a human.

"Cells" mean any cells, including, for example, lung cells, and kidney cells. In the preferred embodiment, the cells are liver cells. In a more preferred embodiment, the cells are human liver cells.

"Attachment" means the state of being firmly attached or bound through chemical or physical interactions or both. "Attachment of hepatitis C virus onto cells" means the hepatitis C virus being firmly attached or bound to the cell surface through the interaction between hepatitis C virus proteins, such as HCV core protein, and the HCV receptors located at the surface of the cells.

"Entry of HCV into cells" means the penetration of hepatitis C virus through the cell membrane into the cells from cell surface.

"Assembly" means association, binding, packing or aggregation. "HCV assembly" means the association of the single stranded HCV RNA with HCV coat proteins, the formation of the single stranded HCV RNA—Coat Protein complex, or the packing of coat proteins onto the single stranded HCV RNA.

"HCV replication" means HCV reproduction within the cells.

"Hepatitis C virus infection" comprises the attachment of hepatitis C virus to cell surface, the entry of hepatitis C virus into cells, the replication of hepatitis C virus within the cells, and the death or transformation of the cells.

"Agent" means any biological molecule which specifically binds to HCV core protein. In one embodiment, the agent comprises a cellular protein.

"Nucleic acid molecule" means any natural or synthetic cDNA or mRNA.

As used herein, "suitable reaction conditions" means conditions under which an agent competitively bind to HCV core protein or a variant thereof.

This invention will be better understood from the Experimental Details which follow. However, one skilled in the art will readily appreciate that the specific methods and results discussed are merely illustrative of the invention as described more fully in the claims which follow thereafter.

Experimental Details

Yeast Two-Hybrid Screening: The Matchmaker Two-Hybrid System 2 was used to screen human liver Matchmaker cDNA library HL4002AB (Clontech) with the cytoplasmic domain (amino acids 1 to 123 that precedes the first predicted transmembrane segment) of HCV core protein as bait in the yeast two-hybrid assay (19). Library screening was performed using previously described methods (20, 29). To construct the bait plasmid, DNA encoding amino acids 1–123 of HCV core protein (numbering as in reference 8) was amplified by PCR with pHCV-1 (12), provided by M. Houghton (Chiron Corporation), as template. The HCV sequences in pHCV-1 derive from a library made from the plasma of an infectious chimpanzee (12). The amplified DNA was cloned into the GAL4 DNA binding domain fusion vector pAS2-1 (Clontech) to yield pAS2-1-HCV-$core_{1-123}$. *Saccharomyces cerevisiae* strain Y190 was sequentially transformed with pAS2-1-HCV-core-123 and library recombinants in the GAL4 activation domain fusion vector pACT2 (Clontech). Positive pACT2-derived plasmids were rescued and used to co-transform yeast with pAS2-1-HCV-core1-123, pLAM5'-1 (Clontech) and pAS2-1 to confirm the specificity of the reactions. For analysis of PL10 and Ded1p binding, cDNAs encoding PL10 from amino acids 408 to 660 and Ded1p amino acids 368 to 604 (corresponding to the longest portion of DBX isolated in the two-hybrid screen) were amplified by PCR from template plasmids (23). The amplified cDNAs were cloned into pACT2 and used to co-transform yeast with pAS2-1-HCV-$core_{1-123}$. DNA sequencing of isolated library plasmid inserts and the bait constructs was performed on a 373A Sequencer (Applied Biosystems) at the Columbia University Cancer Center DNA core facility. Sequence analysis was performed using the Wisconsin Package (Genetics Computer Group) and applications available via the Internet at the National Center for Biotechnology Information World Wide Web site (http://www.ncbi.nlm.nih.gov/).

In Vitro Binding Assays: A PCR product encoding the cytoplasmic domain of HCV core protein (amino acids 1–123) was cloned into pBFT4 for in vitro transcription-translation (26). DBX cDNA encoding amino acids 409 to 662 was excised from plasmid pACT2 by restriction endonuclease digestion and cloned into pGEX2T (Pharmacia Biotech) to yield pGEX2T-DBX409-662 that expressed a glutathione-S-transferase (GST) fusion protein in *Esherichia coli*. Plasmid construction was confirmed by DNA sequencing. In vitro transcription-translation was performed with the TNT T7 Coupled Reticulocyte Lysate System (Promega) using L-[$^{35}$S]-methionine (NEN). Binding assays were performed as described previously (26).

Cell Transfection and Confocal Immunofluorescence Microscopy: A PCR product encoding full-length HCV core protein (amino acids 1–191) obtained using pHCV-1 (12) as template was cloned in-frame into pBFT4 which contains an initiation codon and FLAG tag 5' to the cloning site. A DNA fragment was isolated by restriction endonuclease digestion at sites flanking the initiation and termination codons and cloned into pSVK3 (Pharmacia Biotech) to obtain pSVK3-FLAG-core for expression of HCV core protein with a FLAG tag at its amino-terminus. To obtain full-length DBX cDNA, PCR was performed using a Marathon-ready cDNA human liver library (Clontech) as template to amplify the first 1439 nucleotides of DBX cDNA which was ligated in-frame into pGEX2T-DBX409-662 to produce pGEX2T-DBX. The coding region of pGEX2T-DBX was isolated by restriction endonuclease digestion and cloned into pBluescript II SK$^-$ (Stratagene) to produce pBluescript-DBX. A cDNA containing the 3' 668 nucleotides of DBX, excluding the stop codon, was amplified by PCR and ligated into pBluescript II-DBX to replace the corresponding nucleotides. The entire DBX coding region was then excised by restriction endonuclease digestion and ligated into pcDNA3.1 (−)/Myc-His A (Invitrogen) to produce pcDNA3.1/His A-DBX-myc that encoded full-length DBX with a c-myc tag at its carboxyl-terminus. All plasmid constructs were confirmed by DNA sequencing. Hela or COS-7 cells (ATCC) grown on glass slides were transfected with pSVK3-FLAG-core, pcDNA3.1/HIS A-DBX-myc or both using Tfx-20 (Promega) or DMRIE-C (Life Technologies). Cells were washed in phosphate-buffered saline 48 hours after transfection and fixed with methanol for 5 min at −20° C. followed by acetone at −20° C. for twenty seconds. Indirect immunofluorescence microscopy was performed as described (30). To detect express FLAG-tagged proteins in double-labeling experiments, FLAG-probe (Santa Cruz Biotechnology), a rabbit polyclonal antibody, was used. To reduce background, FLAG-probe was incubated with COS-7 cells fixed with methanol/acetone at a 1:100 dilution for twelve to sixteen hours prior to use. Anti-FLAG M2 monoclonal antibody (Eastman Kodak) was used in single-labeling experiments at a 1:200 dilution. Monoclonal anti-c-myc antibody 9E10 (Babco) was used at a 1:1000 dilution. Fluorescein isothiocyanate-conjugated goat anti-rabbit IgG and rhodamine-conjugated goat anti-mouse IgG secondary antibodies were obtained from Jackson Immuno Research Laboratories. Microscopy was performed using a Zeiss LSM 410 confocal laser scanning system attached to Zeiss Axiovert 100TV inverted microscope (Carl Zeiss). Images were processed using Photoshop software (Adobe) on a Macintosh G3 computer (Apple Computer).

Yeast Strains: Yeast strain YTC83 [MATa ded1::TRP1 ura3-52 lys2-801 ade2-101 trpl-Dl his3-D200 leu2-Dl pPL1004 (PL10/CEN/LEU2)], which contains a chromosomal ded1 deletion complemented by PL10 cDNA (23). To obtain a yeast strain with a chromosomal ded1 deletion complemented by DBX cDNA, full-length DBX cDNA was excised from pGEX2T-DBX by restriction endonuclease digestion and ligated into pRS315pG1. This plasmid was used to transform yeast strain YTC75 [MATa ded1::TRP1 ura3-52 lys2-801 ade2-101 trp1-D1 his3-D200 leu2-Dl pDED1008 (DED1/CEN/URA3)] (23), which was then grown on leucine dropout plates. Transformants were replica-plated onto 5-fluoroorotic acid plates as described (31) to yield strain YNM1DX. To obtain a yeast strain with a chromosomal ded1 deletion complemented by DED1 cDNA driven by a glyceraldehyde-3-phosphate (GPD) promoter on a centromeric plasmid, the native promoter, 5' untranslated region and part of the 5' coding region were excised by restriction endonuclease digestion from pDED1009 (DED1/CEN/LEU2). The GPD promoter, isolated from pRS315pG1 by restriction endonuclease digestion, and 477 5' coding nucleotides of DED1, amplified by PCR, were then sequentially ligated into this pDED1009-derived plasmid to yield pDED$_{GPD}$ Yeast strain YTC75 was then transformed with pDED$_{GPD}$ and 5-fluoroorotic acid counter-selection performed to obtain strain YNM1DD [MAT a ded1::TRP1 ura3-52 lys2-801 ade2-101 trpl-Dl his3-D200 leu2-Dl pDED$_{GPD}$ (DED1/CEN/LEU2)]. All constructs were confirmed by DNA sequencing.

Effects of HCV Core Protein on Growth of Yeast Strains: The coding region for full-length HCV core protein (amino acid 1-191) was excised from pBFT4 by restriction endonuclease digestion and ligated into p423GPD (ATCC) to produce p423GPD-core. The coding region for the cytoplasmic domain of HCV core protein (amino acid 1-123) was also ligated into p423GPD to yield p423GPD-core$_{1-123}$. Constructs were confirmed by DNA sequencing. Yeast strains YTC83, YNM1DX and YNM1DD were transformed with p423GPD, p423GPD-core and p423GPD-core$_{1-123}$ using the lithium acetate-mediated method (24) and grown on histidine-leucine dropout plates for seven days. Plates were photographed to record colony growth.

Effect of HCV Core Protein on In Vitro Translation: cDNA encoding HCV core protein from amino acids 1 to 123 was ligated into pGEX4T-3 (Pharmacia) to produce a GST fusion protein (GST-core$_{1-123}$) in *Esherichia coli*. Plasmid construction was confirmed by DNA sequencing. pGEM-luc (Promega) was linearlized with XhoI and used as a template for luciferase RNA transcription with the RiboMAX RNA Production System-SP6 (Promega). When capped RNA was synthesized, 3 mM of $^7$mGpppG (New England Biolabs) was included in the reaction mixture. The DNA template was removed by digestion with DNase following the transcription reaction and synthesized mRNA was purified using the RNeasy Mini Kit (Qiagen). For in vitro translation, 16.5 μl of Flexi Rabbit Reticulocyte Lysate (Promega) was used and incubated for one hour at 4° C. with 8.25 μl of glutathione-Sepharose 4B (Pharmacia Biotech) loaded with either 300 ng of GST-core-$_{1-123}$ or GST followed by centrifugation for 5 minutes at 2000×g. Translation reactions were then performed according to the manufacturer's instructions and luciferase activity measured by luminescence emission using the Luciferase Assay System (Promega).

HCV Core Protein Binding to DBX: Screening of 8×10$^6$ recombinants of a human liver cell cDNA library with the cytoplasmic domain of HCV core protein as bait in the yeast two-hybrid assay led to the isolation of 5 positive clones, 3 of which encoded portions of DBX, the longest from amino acid 409 to amino acid 662. The two other positive clones encoded portions of epsilon 14-3-3 (See FIG. 4), a member of the 14-3-3 family of proteins that have numerous proposed functions, including activities in signal transduction. DBX is the human orthologue of the mouse DEAD-box protein PL10 (21-22, 32). PL10 is the functional orthologue of *Saccharomyces cerevisiae* Ded1p, an ATP-dependent RNA helicase for capped mRNA (23). DBX is 95% identical in primary structure to PL10 and 54% identical to Ded1p (FIG. 6A). In the yeast two-hybrid assay, HCV core protein interacts with DBX and PL10 but not with Ded1p (FIG. 6B).

Figure 5A:
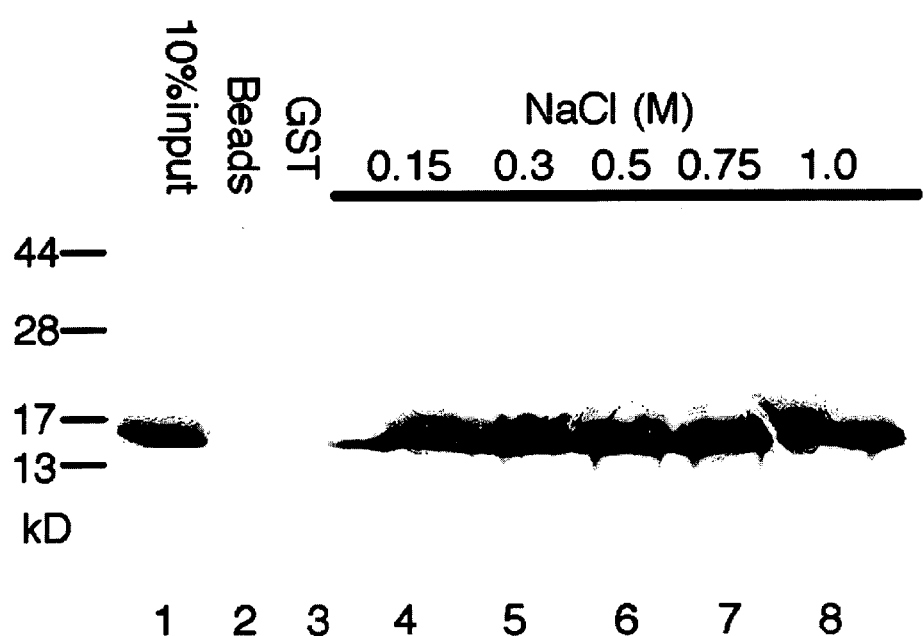
FIG. 5: Binding of DBX to HCV core protein in vitro.
Figure 5B:
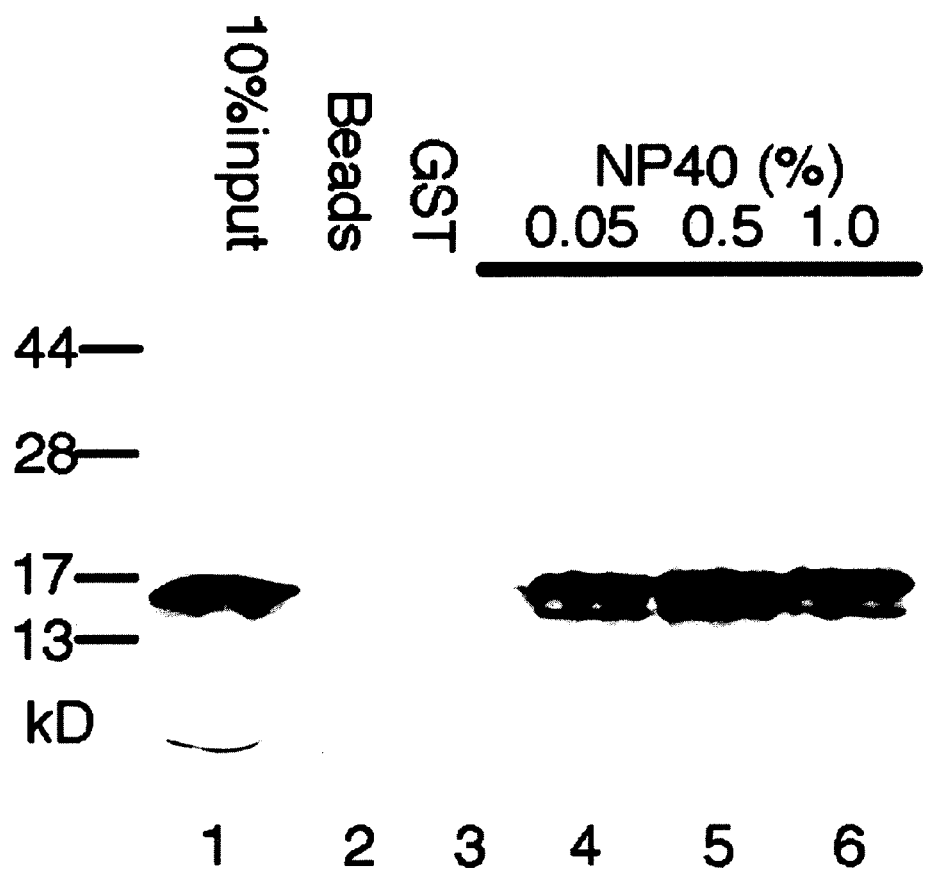

We confirmed the interaction between HCV core protein and DBX in an in vitro binding assay. The cytoplasmic domain of HCV core protein was synthesized by in vitro translation and incubated with GST or a GST-fusion protein containing DBX from amino acid 409 to amino acid 662. Proteins were precipitated with glutathione-Sepharose and HCV core protein binding was analyzed by autoradiography. HCV core protein did not bind to GST but did bind to GST-DBX fusion protein in buffers containing NaCl concentrations as high as 1 Molar (FIG. 5A). Binding also occurred in buffers containing 1% of the non-ionic detergent Nonidet P-40 (FIG. 5B).

Figure 7A:
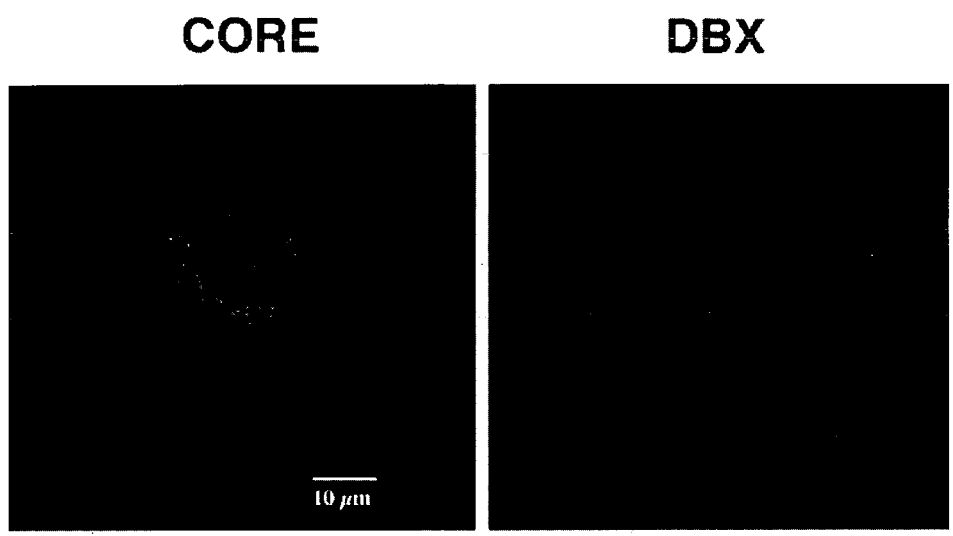
Figure 7B:
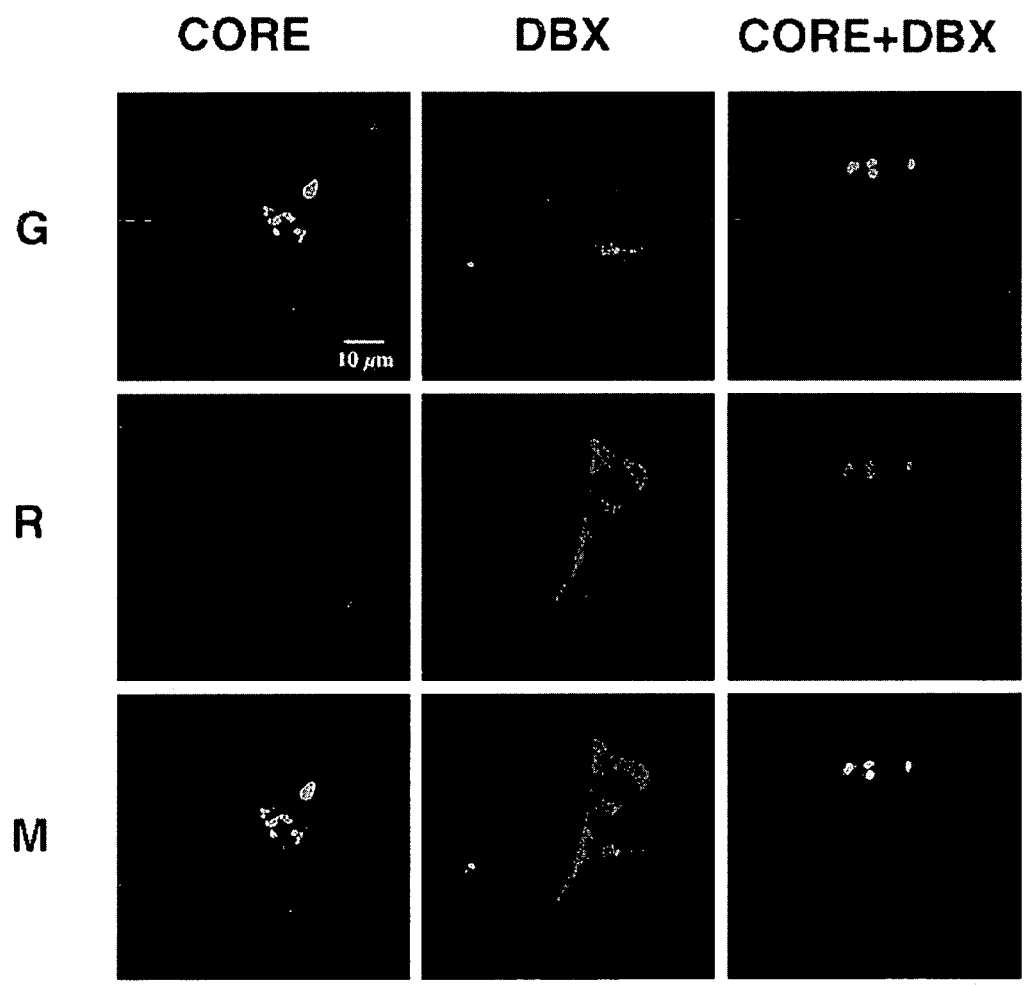

Co-localization of HCV Core Protein and DBX in Cells: An interaction between HCV core protein and DBX in mammalian cells was further supported by their intracellular co-localization. Indirect confocal immunofluorescence microscopy of transfected Hela cells showed that full-length HCV core protein, which contains the cytoplasmic domain and a single transmembrane segment, was localized to the endoplasmic reticulum in discrete foci (FIG. 7A). A similar localization in the endoplasmic reticulum has been reported by others (12). Focal aggregates of HCV core protein likely arise because this polypeptide multimerizes (13). In cells not expressing HCV core protein, DBX had a more diffuse cytoplasmic distribution (FIG. 7A). In cells expressing HCV core protein, however, DBX was found in most instances in discrete foci that co-localized with HCV core protein (FIG. 7B). The antibodies used to detect the respective epitope tags of each protein did not cross-react significantly (FIG. 7B). HCV core protein therefore forms aggregates at the endoplasmic reticulum membrane with which DBX apparently associates.

DBX Rescues Ded1-deletion Yeast Mutants and Rescue is Prevented by HCV Core: DBX likely functions as an ATP-dependent RNA helicase for cellular mRNA, which can be inferred from its sequence similarity to mouse PL10 and yeast Ded1p (22–23). To examine the effect of HCV core protein on DBX function, we took advantage of yeast genetics and the fact that *Saccharomyces cerevisiae* has only one essential DBX-like protein, Ded1p (23). When driven by a yeast GPD promoter and carried on a centromere plasmid, mouse PL10 cDNA, as previously described (23), and DBX cDNA rescued the lethality of cells with a chromosomal ded1 deletion. This indicates that DBX can likely function as a RNA helicase as it can replace the function of the yeast DEAD-box RNA helicase Ded1p. Expression of full-length HCV core protein severely inhibited the growth of DBX- and PL10- complemented ded1-deletion yeast but not ded1-deletion yeast complemented with DED1 cDNA driven by the same promoter on a centromeric plasmid (FIG. 8). This is consistent with the observation that DBX and PL10, but not Ded1p, bind to HCV core protein. The cytoplasmic domain of HCV core protein that binds to DBX, without a transmembrane segment, did not significantly inhibit the growth of DBX- and PL10- complemented ded1-deletion yeast (data not shown), suggesting that inhibition of function may result from trapping of these proteins in aggregates at the endoplasmic reticulum membrane (see FIG. 7).

Inhibition of In Vitro Translation of Capped mRNA by HCV Core Protein: We examined the effects of HCV core protein on the translation of capped and uncapped luciferase RNA in an in vitro reticulocyte lysate assay. If HCV inhibits DBX's function as a RNA helicase, it should theoretically decrease the translation of capped RNA while but not significantly affect the translation of uncapped RNA. In the in vitro translation assay, the cytoplasmic portion of HCV core protein significantly inhibited the in vitro translation of luciferase from capped but not uncapped RNA (FIG. 9). Capped RNA translation was approximately four-fold higher than uncapped RNA translation in this assay (data not shown). This finding suggests that HCV core protein may inhibit the translation of capped mRNA in cells, presumably by inhibiting DBX function.

HCV core protein binds to the human DEAD-box protein DBX: DBX rescues the lethal phenotype of ded1-deletion demonstrating that it can function as a RNA helicase for capped mRNA, replacing the essential yeast DEAD-box RNA helicase Ded1p. Our findings that HCV core protein prevents DBX from rescuing ded1-deletion yeast and that it inhibits the translation of capped RNA in vitro strongly suggest that it may inhibit cellular mRNA translation in vivo. These results, however, cannot establish if translation inhibition occurs as a result of HCV core protein inhibiting DBX RNA helicase activity per se or by an interaction that results in trapping DBX at a location near the membrane of the endoplasmic reticulum where it cannot function properly. Inhibition of host cell mRNA translation could theoretically provide viral RNA molecules with enhanced access to ribosomes and the rest of the cell's protein synthesis machinery, a phenomenon shared by several different viruses (33). A recent report has shown that high levels of expression of HCV structural and non-structural proteins is toxic to mammalian cells (34), however, it is not clear if this toxicity results from inhibition of host cell translation. Because the development of a robust cell culture system to study HCV has remained elusive, it would be extremely difficult to directly investigate the effects of HCV infection on host cell mRNA translation. Despite these methodological constraints limiting the ability to directly test the hypothesis, our discovery that HCV core binds to DBX and inhibits capped RNA translation in experimental assays suggests that it can similarly inhibit mRNA translation in infected human cells.

DEAD-box RNA helicases unwind capped mRNA (23) and inhibition of their function should decrease translation of cellular mRNA. Inhibition of DBX function by HCV core protein may only partially inhibit host mRNA translation in mammalian cells because they contain other putative RNA helicases (35). In contrast, the translation of HCV RNA, which is not capped, utilizes internal ribosome entry sites (10, 11) and can be unwound by its own RNA helicase that is part of the HCV NS3 protein (36, 37), may proceed without DBX. This hypothetical mechanism is reminiscent of that used by poliovirus which inhibits translation factor eIF-4F (38, 39) and also has RNA with internal ribosome entry sites (40). In cells, eIF-4F exists as a complex with eIF-4B, which has RNA binding activity, and eIF-4A, which is also a DEAD-box RNA helicase (41). HCV and poliovirus infection may both therefore cause a decrease in the unwinding of capped mRNA in host cells.

In addition to inhibiting capped mRNA translation in infected host cells, the interaction between HCV core protein and DBX may play other possible roles, including the recruitment of DBX to participate in HCV replication itself. Recruitment of host cells proteins into virions to enhance viral replication has been demonstrated in other systems. For example, the principal structural protein of the human immunodeficiency virus HIV-1 binds to cyclophilins and recruits cyclophilin A into viral particles, which appears to be necessary for efficient viral replication (42, 43). In a similar fashion, recruitment of DBX into HCV particles by binding to core protein may enhance viral replication. This could theoretically occur by DBX altering viral genomic RNA structure in viral particles of in newly infected cells. Testing of this hypothesis is limited at the present time because of the lack of an efficient cell culture system for HCV.

HCV core protein has also been shown to bind to lymphotoxin-β receptor and other tumor necrosis factor receptor family members (15, 27) as well as ribonucleoprotein K (28). In our yeast two-hybrid screen, we did not isolate clones for these proteins, possibly because of subtle differences in our bait construct and the different cDNA library we used. The demonstration that other proteins interact with HCV core protein suggests that its expression in cells may have myriad consequences. Other groups (18, 44) have also reported that HCV core protein represses transcription from the p53 promoter and other eukaryotic promoters. The overall effect of HCV core protein on cell physiology under natural conditions of infection is, however, difficult to assess at the present time because of lack of a cell culture system for HCV.

Finally, it should be noted that the best current treatment regimens for chronic hepatitis C are effective in only a minority of patients (45). If interactions between HCV and host cell proteins alter cell survival or enhance viral replication, they could be rational targets for antiviral drug design. Regardless of the physiological significance, the tight binding of any polypeptide to a structural or non-structural protein of HCV may potentially interfere with viral replication. The identification of polypeptides such as DBX that bind to HCV proteins therefore has implications for the design of compounds which may be therapeutically useful in the treatment of patients with chronic hepatitis C.

Compounds that specifically target HCV can be developed to treat HCV infection. Possible targets are the HCV proteases, RNA helicase and RNA polymerase. As the three-dimensional structures of the NS3 protease and helicase are known, rational drug design in combination with combinatorial chemistry may lead to the development of inhibitors. Other possible targets are the 5' untranslated region of the viral RNA that uses a different mechanism of ribosome entry than most host cell RNAs. The major viral structural protein (core protein, envelope proteins E1 and E2) can also be targeted for treating HCV infection. Inhibitors of core protein and envelope protein binding to critical cellular proteins could also useful therapeutic agents.

REFERENCES

1. Mamiya, N., and Worman, H. J. (1997) "Epidemiology, prevention, clinical features and therapy of hepatitis B, C and G." *Curr. Opin. Infect. Dis.,* 10:3990–397;
2. Alter, M. J. (1997) "Epidemiology of hepatitis C." *Hepatology,* 26:62S–65S;
3. Choo, Q.-L., et al. (1989) "Isolation of a cDNA clone derived from blood-borne nonA, nonB viral hepatitis genome" *Science,* 244:359–362;
4. Kuo, G., et al. (1989) "An assay for circulating antibodies to a major etiological virus of human non-A, non-B hepatitis" *Science,* 244:359–363;
5. National Institutes of Health Consensus Development Conference Panel Statement (1997) "Management of Hepatitis C" *Hepatology,* 26:2S–10S;
6. Kato, N., et. al. (1990) "Molecular cloning of the human hepatitis C virus genome from Japanese patients with non-A, non-B hepatitis" *Proc. Natl. Acad. Sci. U.S.A.,* 87:9524–9528;
7. Choo, Q.-L., et al. (1991) "Genetic organization and diversity of the hepatitis C virus" *Proc. Natl. Acad. Sci. U.S.A.,* 88:2451–2455;
8. Okamoto, H., et al. (1991) "Nucleotide sequence of the genomic RNA hepatitis C virus isolated from a human carrier: comparison with reported isolates from conserved and divergent regions" *J. Gen. Virol.,* 72:2697–6704;
9. Takamizawa, A., et al. (1991) "Structure and organization of the hepatitis C genome isolated from human carriers" *J. Viol.,* 65:1105–1113;
10. Reynolds, J. E., et al. (1995) "Unique features of internal initiation of hepatitis C virus RNA translation" *EMBO J.,* 14:6010–6020;
11. Fukushi, S., et al. (1997) "The sequence element of the internal ribosome entry site and a 25-kilodalton cellular protein contribute to efficient internal initiation of translation of hepatitis C virus RNA" *J. Virol.,* 71:1662–1666;
12. Selby, M. J., et al. (1993) "Expression, identification and subcellular localization of the proteins encoded by the hepatitis C viral genome" *J. Gen. Virol.,* 74:1103–1113;
13. Matsumoto, M., et al. (1996) "Homotypic interactions and multimerization of the hepatitis C virus core protein" *Virology.,* 218:43–51;
14. Ray, R. B., et al. (1996) "Hepatitis C virus core protein cooperates with ras and transforms primary rat embryo fibroblasts to tumorigenic phenotype" *J. Virol.,* 70:4438–4443;
15. Matsumoto, M., et al. (1997) "Hepatitis C virus core protein interacts with the cytoplasmic tail of lymphotoxin-β receptor" *J. Virol.,* 71:1301–1309;
16. Lanford, R. E., et al. (1993) "Analysis of hepatitis C virus capsid, E1, and E2/NS1 proteins expressed in insect cells" *Virology,* 197:225–235;
17. Suzuki, R., et al. "Nuclear localization of the truncated hepatitis C virus core protein with its hydrophobic C terminus deleted" *J. Gen. Virol.,* 76:53–61;
18. Ray, R. B., et al. (1997) "Transcriptional repression of p53 promoter by hepatitis C virus core protein" *J. Biol. Chem.,* 272:10983–10986;
19. Fields, S., and Song, O. (1989) "A novel genetic system to detect protein—protein interactions" *Nature,* 340:245–246;
20. Chien, C., et al. (1991) "The two-hybrid system: a method to identify and clone genes for proteins that interact with a protein of interest" *Proc. Natl. Acad. Sci. U.S.A.,* 88:9578–9582;
21. Lahn, B. T., and Page, D. C. (1997) "Functional coherence of the human Y chromosome" *Science,* 278:675–680;
22. Leroy, P., et al. (1989) "The protein encoded by a murine male germ cell-specific transcript is a putative ATP-dependent RNA helicase" *Cell,* 57:549–559;
23. Chuang, R.-Y., et al. (1997) "Requirement of the DEAD-box protein Ded1p for messenger RNA translation" *Science,* 275:1468–1471;
24. Saiki, R. K., et al. (1988) "Primer-directed enzymatic amplification of DNA with a thermostable DNA polymerase" *Science,* 239:487–491;
25. Smith, D. B. and Johnson, K. S. (1988) "Single-step purification of polypeptides expressed in *Escherichia coli* as fusions with glutathione-S-transferase" *Gene.,* 67:31–40;

26. Ye, Q., and Worman, H. J. (1996) "Interaction between an integral protein of the nuclear envelope inner membrane and human chromodomain proteins homologous to *Drosophila* HP1" *J. Biol. Chem.*, 271:14653–14656;
27. Zhu, N., et al. (1998) *J. Virol.* 72, 3691–3697;
28. Hsieh, T.-Y., et al. (1998) *J. Biol. Chem.*, 271, 17651–17659;
29. Durfee, T., Becherer, K., Chen, P. L., Yeh, S. H., Yang, Y., Kilburn, A. E., Lee, W. H., and Elledge, S. J. (1993) *Genes Dev.* 7, 555–569;
30. Soullam, B., and Worman, H. J. (1995) *J. Cell Biol.* 130, 15–27;
31. Boeke, J. D., Trueheart, J., Natsoulis, G., and Fink, G. R. (1987) *Methods Enzymol.* 154, 164–175;
32. Chung, J., Lee, S., and Song, K. (1995) *Korean J. Biochem.* 27, 193–197;
33. Knipe, D. M. (1996) in *Field's Virology*, eds. Fields, B. N., Knipe, D. M., and Howley, P. M. (Lippincott-Raven Publishers, Philadelphia), 3rd Ed., pp. 273–299;
34. Moradpour, D., Kary, P., Rice, C. M., and Slum, H. E. (1998) *Hepatology*, 28, 192–201;
35. Gee, S. L., and Conboy, J. G. (1994) *Gene*, 140: 171–177;
36. Yao, N., et al. (1997) *Nat. Struct. Biol.*, 4: 463–467;
37. Kim, J. L., et al. (1998) *Structure*, 6: 89–100;
38. Rose, J. K., et al. (1978) *Proc. Natl. Acad. Sci. U.S.A.*, 75: 2732–2736;
39. Etchison, D., et al. (1982) *J. Biol. Chem.*, 14806–14810;
40. Pelletier, J., and Sonenberg, N. (1988) *Nature*, 334: 320–325;
41. Rozen, F., et al. (1990) *Mol. Cell Biol.*, 10: 1134–1144;
42. Luban, J., et al. (1993) *Cell*, 18: 1067–1078;
43. Franke, E. K., et al. (1994) *Nature*, 372: 359–362;
44. Kim, D. W., et al. (1994) *Jpn. J. Med. Sci. Biol.*, 47: 211–220; and
45. Liang, T. J. (1998) *N. Eng. J. Med.*, 339: 1549–1550.

What is claimed is:

1. A method of treating hepatitis C virus infection in a subject which comprises administering to the subject an effective amount of a DEAD-box protein capable of specifically binding to the HCV core protein so as to inhibit hepatitis C virus replication.

2. The method of claim 1, wherein the hepatitis C virus infects the liver of the subject.

3. The method of claim 1, wherein the hepatitis C virus infects the liver of a human.

4. The method of claim 1, wherein the DEAD-box protein comprises a DEAD-box RNA helicase.

5. The method of claim 4, wherein the DEAD-box RNA helicase comprises a human DEAD-box protein DBX or a variant thereof.

6. The method of claim 5, wherein the human DEAD-box protein DBX comprises amino acids having the amino acid sequence SEQ ID NO:1.

7. The method of claim 5, wherein the variant of the human DEAD-box protein DBX comprises amino acids having the amino acid sequence SEQ ID NO:2.

8. The method of claim 5, wherein the variant of the human DEAD-box protein DBX comprises amino acids having the amino acid sequence SEQ ID NO:3.

9. The method of claim 5, wherein the variant of the human DEAD-box protein DBX comprises 100–200 amino acid residues of the amino acid sequence SEQ ID NO:1 or the amino acid sequence SEQ ID NO:3.

* * * * *